United States Patent
Krauss et al.

(10) Patent No.: US 9,322,833 B2
(45) Date of Patent: Apr. 26, 2016

(54) ULTRA-SMALL APOB-CONTAINING PARTICLES AND METHODS OF USE THEREOF

(75) Inventors: Ronald M. Krauss, Berkeley, CA (US); Mohmed Elfatih Ashmaig, Richmond, VA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 0 days.

(21) Appl. No.: 14/123,927

(22) PCT Filed: Jun. 14, 2012

(86) PCT No.: PCT/US2012/042513
§ 371 (c)(1),
(2), (4) Date: Apr. 16, 2014

(87) PCT Pub. No.: WO2012/174278
PCT Pub. Date: Dec. 20, 2012

(65) Prior Publication Data
US 2015/0126473 A1    May 7, 2015

Related U.S. Application Data

(60) Provisional application No. 61/497,847, filed on Jun. 16, 2011.

(51) Int. Cl.
*C07K 14/775* (2006.01)
*G01N 33/68* (2006.01)
*C07K 14/47* (2006.01)
*B82Y 15/00* (2011.01)
*G01N 33/92* (2006.01)
*B82Y 5/00* (2011.01)

(52) U.S. Cl.
CPC ............ *G01N 33/6893* (2013.01); *B82Y 15/00* (2013.01); *C07K 14/4741* (2013.01); *C07K 14/775* (2013.01); *G01N 33/6887* (2013.01); *G01N 33/92* (2013.01); *B82Y 5/00* (2013.01); *G01N 2333/4742* (2013.01); *G01N 2333/775* (2013.01); *G01N 2800/32* (2013.01); *G01N 2800/52* (2013.01); *Y10T 428/2982* (2015.01)

(58) Field of Classification Search
CPC ..................................................... C07K 14/775
See application file for complete search history.

(56) References Cited

U.S. PATENT DOCUMENTS

| 5,925,229 A * | 7/1999 | Krauss et al. ................. 204/606 |
| 7,259,018 B2 * | 8/2007 | Benner et al. ................... 436/71 |
| 7,713,744 B2 * | 5/2010 | Benner et al. ................... 436/71 |
| 2008/0038829 A1 | 2/2008 | Kremer et al. |
| 2009/0317819 A1 | 12/2009 | Tsimikas et al. |
| 2010/0323376 A1 | 12/2010 | Contois |

OTHER PUBLICATIONS

Al-Bahrani, et al.; "A potential role of apolipoprotein B in the risk stratification of diabetic patients with dyslipidaemia"; Diabetes Research and Clinical Practice; vol. 69, No. 1, pp. 44-51 (Jul. 2005).
Katsuda, et al.; "Human Atherosclerosis: Immunocytochemical Analysis of the Cell Composition of Lesions of Young Adults"; American Journal of Pathology; vol. 140, No. 4, pp. 907-914 (Apr. 1992).
Koba, et al.; "Significance of small dense low-density lipoproteins and other risk factors in patients with various types of coronary heart disease"; Am. Heart. J.; vol. 144, No. 6, pp. 1026-1035 (2002).
Ogasawara, et al; "Low-density lipoprotein (LDL), which includes apolipoprotein A-I (apoAI-LDL) as a novel marker of coronary artery disease"; Clinica Chimica Acta; vol. 397, pp. 42-47 (2008).

* cited by examiner

*Primary Examiner* — Karlheinz R Skowronek
(74) *Attorney, Agent, or Firm* — Bozicevic Field & Francis, LLP; Paula Borden; Makoto Tsunozaki

(57) ABSTRACT

The present disclosure provides an isolated particle comprising very high density, ultra small, lipid depleted apo B containing particles, and may also contain cytokeratin 8. The isolated particle is useful in diagnostic assays, which are also provided.

32 Claims, 16 Drawing Sheets apoB-100
GenBank NP_000375.2

```
   1  mdpprpalla llalpallll llagaraeee mlenvslvcp kdatrfkhlr kytynyeaes
  61  ssgvpgtads rsatrinckv elevpqlcsf ilktsqctlk evygfnpegk allkktknse
 121  efaaamsrye lklaipegkq vflypekdep tyilnikrgi isallvppet eeakqvlfld
 181  tvygncsthf tvktrkgnva teisterdlg qcdrfkpirt gisplalikg mtrplstlis
 241  ssqscqytld akrkhvaeai ckeqhlflpf syknkygmva qvtqtlkled tpkinsrffg
 301  egtkkmglaf estkstsppk qaeavlktlq elkkltiseq niqranlfnk lvtelrglsd
 361  eavtslIpql ievsspitlq alvqcgqpqc sthilqwlkr vhanpllidv vtylvalipe
 421  psaqqlreif nmardqrsra tlyalshavn nyhktnptgt qelldianyl meqiqddctg
 481  dedytylilr vignmgqtme qltpelkssi lkcvqstkps lmiqkaaiqa lrkmepkdkd
 541  qevllqtfld daspgdkrla aylmlmsps qadinkivqi lpweqneqvk nfvashiani
 601  lnseeldiqd lkklvkealk esqlptvmdf rkfsrnyqly ksvslpsldp asakiegnli
 661  fdpnnylpke smlkttltaf gfasadliei glegkgfept lealfgkqgf fpdsvnkaly
 721  wvngqvpdgv skvlvdhfgy tkddkheqdm vngimlsvek likdlkskev pearaylril
 781  geelgfaslh dlqllgklll mgartlqgip qmigevirkg skndfflhyi fmenafelpt
 841  gaglqlqiss sgviapgaka gvklevanmq aelvakpsvs vefvtnmgii ipdfarsgvq
 901  mntnffhesg leahvalkag klkfiipspk rpvkllsggn tlhlvsttkt evipplienr
 961  qswsvckqvf pglnyctsga ysnasstdsa syypltgdtr lelelrptge ieqysvsaty
1021  elqredralv dtlkfvtqae gakqteatmt fkynrqsmtl ssevqipdfd vdlgtilrvn
1081  destegktsy rltldiqnkk itevalmghl scdtkeerki kgvisiprlq aearseilah
1141  wspaklllqm dssataygst vskrvawhyd eekiefewnt gtnvdtkkmt snfpvdlsdy
```

FIG. 17A

```
1201 pkslhmyanr lldhrvpqtd mtfrhvgskl ivamsswlqk asgslpytqt lqdhlnslke
1261 fnlqnmglpd fhipenlflk sdgrvkytln knslkieipl pfggkssrdl kmletvrtpa
1321 lhfksvgfhl psrefqvptf tipklyqlqv pllgvldlst nvysnlynws asysggntst
1381 dhfslraryh mkadsvvdll synvqgsget tydhkntftl scdgslrhkf ldsnikfshv
1441 eklgnnpvsk gllifdasss wgpqmsasvh ldskkkqhlf vkevkidgqf rvssfyakgt
1501 yglscqrdpn tgrlngesnl rfnssylqgt nqitgryedg tlsltstsdl qsgiikntas
1561 lkyenyeltl ksdtngkykn fatsnkmdmt fskqnallrs eyqadyeslr ffsllsgsln
1621 shglelnadi lgtdkinsga hkatlriggd gistsattnl kcsllvlene lnaelglsga
1681 smklttngrf rehnakfsld gkaaltelsl gsayqamilg vdsknifnfk vsqeqlklsn
1741 dnmgsyaemk fdhtnslnia glsldfsskl dniyssdkfy kqtvnlqlqp yslvttlnsd
1801 lkynaldltn ngklrleplk lhvagnlkga yqnneikhiy aissaalsas ykadtvakvq
1861 gvefshrlnt diaglasaid mstnynsdsl hfsnvfrsvm apftmtidah tngngklalw
1921 gehtgqlysk fllkaeplaf tfshdykgst shhlvsrksi saalehkvsa lltpaeqtgt
1981 wklktqfnnn eysqdldayn tkdkigvelt grtladltl dspikvplll sepiniidal
2041 emrdavekpq eftivafvky dknqdvhsin lpffetlqey fernrqtiiv vlenvqrnlk
2101 hinidqfvrk yraalgklpq qandylnsfn werqvshake kltaltkkyr itendiqial
2161 ddakinfnek lsqlqtymiq fdqyikdsyd lhdlkiaian iideiieklk sldehyhirv
2221 nlvktihdlh lfienidfnk sgsstaswiq nvdtkyqiri qiqeklqqlk rhiqnidiqh
2281 lagklkqhie aidvrvlldq lgttisferi ndvlehvkhf vinligdfev aekinafrak
2341 vhelieryev dqqiqvlmdk lvelahqykl ketiqklsnv lqqvkikdyf eklvgfidda
2401 vkklnelsfk tfiedvnkfl dmlikklksf dyhqfvdetn dkirevtqrl ngeiqalelp
2461 qkaealklfl eetkatvavy leslqdtkit liinwlqeal ssaslahmka kfretledtr
```

```
2521 drmyqmdiqq elqrylslvg qvystlvtyi sdwwtlaakn ltdfaeqysi qdwakrmkal
2581 veqgftvpei ktilgtmpaf evslqalqka tfqtpdfivp ltdlripsvq infkdlknik
2641 ipsrfstpef tilntfhips ftidfvemkv kiirtidqml nselqwpvpd iylrdlkved
2701 iplaritlpd frlpeiaipe fiiptlnlnd fqvpdlhipe fqlphishti evptfgklys
2761 ilkiqsplft ldanadigng ttsaneagia asitakgesk levlnfdfqa naqlsnpkin
2821 plalkesvkf sskylrtehg semlffgnai egksntvasl hteknlels ngvivikinnq
2881 ltldsntkyf hklnipkldf ssqadlrnei ktllkaghia wtssgkgswk wacprfsdeg
2941 thesqisfti egpltsfgls nkinskhlrv nqnlvyesgs lnfskleiqs qvdsqhvghs
3001 vltakgmalf gegkaeftgr hdahlngkvi gtlknslffs aqpfeitast nnegnlkvrf
3061 plrltgkidf lnnyalflsp saqqaswqvs arfnqykynq nfsagnneni meahvginge
3121 anldflnipl tipemrlpyt iittpplkdf slwektglke flkttkqsfd lsvkaqykkn
3181 khrhsitnpl avlcefisqs iksfdrhfek nrnnaldfvt ksynetkikf dkykaekshd
3241 elprtfqipg ytvpvvnvev spftiemsaf gyvfpkavsm psfsilgsdv rvpsytlilp
3301 slelpvlhvp rniklslpdf kelctishif ipamgnityd fsfkssvitl ntnaelfnqs
3361 divahlsss ssvidalqyk legttrltrk rglklatals lsnkfvegsh nstvslttkn
3421 mevsvatttk aqipilrmnf kqelngntks kptvsssmef kydfnssmly stakgavdhk
3481 lslesltsyf siesstkgdv kgsvlsreys gtiaseanty lnskstrssv klqgtskidd
3541 iwnlevkenf ageatlqriy slwehstknh lqleglfftn gehtskatle lspwqmsalv
3601 qvhasqpssf hdfpdlgqev alnantknqk irwknevrih sgsfqsqvel sndqekahld
3661 iagsleghlr flkniilpvy dkslwdflkl dvttsigrrq hlrvstafvy tknpngysfs
3721 ipvkvladkf iipglklndl nsvlvmptfh vpftdlqvps ckldfreiqi ykklrtssfa
3781 lnlptlpevk fpevdvltky sqpedslipf feitvpesql tvsqftlpks vsdgiaaldl
3841 navankiadf elptiivpeq tieipsikfs vpagivipsf qaltarfevd spvynatwsa
```

```
3901 slknkadyve tvldstcsst vqfleyelnv lgthkiedgt lasktkgtfa hrdfsaeyee
3961 dgkyeglqew egkahlniks paftdlhlry qkdkkgists aaspavgtvg mdmdeddfs
4021 kwnfyyspqs spdkkltifk telrvresde etqikvnwee eaasglltsl kdnvpkatgv
4081 lydyvnkyhw ehtgltlrev ssklrrnlqn naewvyqgai rqiddidvrf qkaasgttgt
4141 yqewkdkaqn lyqelltqeg qasfqglkdn vfdglvrvtq efhmkvkhli dslidflnfp
4201 rfqfpgkpgi ytreelctmf irevgtvlsq vyskvhngse ilfsyfqdlv itlpfelrkh
4261 klidvismyr ellkdlskea qevfkaiqsl kttevlrnlq dllqfifqli edniqklkem
4321 kftylinyiq deintifsdy ipyvfkllke nlclnlhkfn efiqnelqea sqelqqihqy
4381 imalreeyfd psivgwtvky yeleekivsl iknllvalkd fhseyivsas nftsqlssqv
4441 eqflhrniqe ylsiltdpdg kgkekiaels ataqeiiksq aiatkkiisd yhqqfryklq
4501 dfsdqlsdyy ekfiaeskrl idlsiqnyht fliyitellk klqsttvmnp ymklapgelt
4561 iil (SEQ ID NO:1)
```

FIG. 17D

***Homo sapiens* cytokeratin 8**
GenBank AAA35763

```
  1 msirvtqksy kvstsgpraf ssrsytsgpg srissssfsr vgssnfrggl gggyggasgm
 61 ggitavtvnq sllsplvlev dpniqavrtq ekeqiktlnn kfasfidkvr fleqqnkmle
121 tkwsllqqqk tarsnmdnmf esyinnlrrq letlgqeklk leaelgnmqg lvedfknkye
181 deinkrteme nefvlikkdv deaymnkvel esrlegltde inflrqlyee eirelqsqis
241 dtsvvlsmdn srsldmdsii aevkaqyedi anrsraeaes myqikyeelq slagkhgddl
301 rrtkteisem nrnisrlqae ieglkgqras leaaiadaeq rgelaikdan aklseleaal
361 qrakqdmarq lreyqelmnv klaldieiat yrkllegees rlesgmqnms ihtkttggya
421 gglssayggs qaglsyslgs sfgsgagsss fsrtsssrav vvkkietrdg klvsessdvl
481 pk (SEQ ID NO:2)
```

FIG. 18

SEQUENCE LISTING

```
<160> NUMBER OF SEQ ID NOS: 2

<210> SEQ ID NO 1
<211> LENGTH: 4563
<212> TYPE: PRT
<213> ORGANISM: Homo sapiens

<400> SEQUENCE: 1

Met Asp Pro Pro Arg Pro Ala Leu Leu Ala Leu Leu Ala Leu Pro Ala
1               5                   10                  15

Leu Leu Leu Leu Leu Leu Ala Gly Ala Arg Ala Glu Glu Glu Met Leu
                20                  25                  30

Glu Asn Val Ser Leu Val Cys Pro Lys Asp Ala Thr Arg Phe Lys His
            35                  40                  45

Leu Arg Lys Tyr Thr Tyr Asn Tyr Glu Ala Glu Ser Ser Ser Gly Val
        50                  55                  60
```

```
Pro Gly Thr Ala Asp Ser Arg Ser Ala Thr Arg Ile Asn Cys Lys Val
 65                  70                  75                  80

Glu Leu Glu Val Pro Gln Leu Cys Ser Phe Ile Leu Lys Thr Ser Gln
                 85                  90                  95

Cys Thr Leu Lys Glu Val Tyr Gly Phe Asn Pro Glu Gly Lys Ala Leu
            100                 105                 110

Leu Lys Lys Thr Lys Asn Ser Glu Glu Phe Ala Ala Ala Met Ser Arg
        115                 120                 125

Tyr Glu Leu Lys Leu Ala Ile Pro Glu Gly Lys Gln Val Phe Leu Tyr
    130                 135                 140

Pro Glu Lys Asp Glu Pro Thr Tyr Ile Leu Asn Ile Lys Arg Gly Ile
145                 150                 155                 160

Ile Ser Ala Leu Leu Val Pro Pro Glu Thr Glu Glu Ala Lys Gln Val
                165                 170                 175

Leu Phe Leu Asp Thr Val Tyr Gly Asn Cys Ser Thr His Phe Thr Val
            180                 185                 190

Lys Thr Arg Lys Gly Asn Val Ala Thr Glu Ile Ser Thr Glu Arg Asp
        195                 200                 205

Leu Gly Gln Cys Asp Arg Phe Lys Pro Ile Arg Thr Gly Ile Ser Pro
    210                 215                 220

Leu Ala Leu Ile Lys Gly Met Thr Arg Pro Leu Ser Thr Leu Ile Ser
225                 230                 235                 240

Ser Ser Gln Ser Cys Gln Tyr Thr Leu Asp Ala Lys Arg Lys His Val
                245                 250                 255

Ala Glu Ala Ile Cys Lys Glu Gln His Leu Phe Leu Pro Phe Ser Tyr
            260                 265                 270

Lys Asn Lys Tyr Gly Met Val Ala Gln Val Thr Gln Thr Leu Lys Leu
        275                 280                 285

Glu Asp Thr Pro Lys Ile Asn Ser Arg Phe Phe Gly Glu Gly Thr Lys
    290                 295                 300

Lys Met Gly Leu Ala Phe Glu Ser Thr Lys Ser Thr Ser Pro Pro Lys
305                 310                 315                 320

Gln Ala Glu Ala Val Leu Lys Thr Leu Gln Glu Leu Lys Lys Leu Thr
                325                 330                 335

Ile Ser Glu Gln Asn Ile Gln Arg Ala Asn Leu Phe Asn Lys Leu Val
            340                 345                 350

Thr Glu Leu Arg Gly Leu Ser Asp Glu Ala Val Thr Ser Leu Leu Pro
        355                 360                 365

Gln Leu Ile Glu Val Ser Ser Pro Ile Thr Leu Gln Ala Leu Val Gln
    370                 375                 380

Cys Gly Gln Pro Gln Cys Ser Thr His Ile Leu Gln Trp Leu Lys Arg
385                 390                 395                 400

Val His Ala Asn Pro Leu Leu Ile Asp Val Val Thr Tyr Leu Val Ala
                405                 410                 415

Leu Ile Pro Glu Pro Ser Ala Gln Gln Leu Arg Glu Ile Phe Asn Met
            420                 425                 430

Ala Arg Asp Gln Arg Ser Arg Ala Thr Leu Tyr Ala Leu Ser His Ala
        435                 440                 445

Val Asn Asn Tyr His Lys Thr Asn Pro Thr Gly Thr Gln Glu Leu Leu
    450                 455                 460

Asp Ile Ala Asn Tyr Leu Met Glu Gln Ile Gln Asp Asp Cys Thr Gly
465                 470                 475                 480

Asp Glu Asp Tyr Thr Tyr Leu Ile Leu Arg Val Ile Gly Asn Met Gly
```

```
                485               490               495
Gln Thr Met Glu Gln Leu Thr Pro Glu Leu Lys Ser Ser Ile Leu Lys
                500               505               510
Cys Val Gln Ser Thr Lys Pro Ser Leu Met Ile Gln Lys Ala Ala Ile
                515               520               525
Gln Ala Leu Arg Lys Met Glu Pro Lys Asp Lys Gln Glu Val Leu
            530               535           540
Leu Gln Thr Phe Leu Asp Asp Ala Ser Pro Gly Asp Lys Arg Leu Ala
545             550               555               560
Ala Tyr Leu Met Leu Met Arg Ser Pro Ser Gln Ala Asp Ile Asn Lys
                565               570               575
Ile Val Gln Ile Leu Pro Trp Glu Gln Asn Glu Gln Val Lys Asn Phe
                580               585               590
Val Ala Ser His Ile Ala Asn Ile Leu Asn Ser Glu Glu Leu Asp Ile
                595               600               605
Gln Asp Leu Lys Lys Leu Val Lys Glu Ala Leu Lys Glu Ser Gln Leu
                610               615               620
Pro Thr Val Met Asp Phe Arg Lys Phe Ser Arg Asn Tyr Gln Leu Tyr
625                 630               635               640
Lys Ser Val Ser Leu Pro Ser Leu Asp Pro Ala Ser Ala Lys Ile Glu
                    645               650               655
Gly Asn Leu Ile Phe Asp Pro Asn Asn Tyr Leu Pro Lys Glu Ser Met
                660               665               670
Leu Lys Thr Thr Leu Thr Ala Phe Gly Phe Ala Ser Ala Asp Leu Ile
                675               680               685
Glu Ile Gly Leu Glu Gly Lys Gly Phe Glu Pro Thr Leu Glu Ala Leu
690               695               700
Phe Gly Lys Gln Gly Phe Phe Pro Asp Ser Val Asn Lys Ala Leu Tyr
705               710               715               720
Trp Val Asn Gly Gln Val Pro Asp Gly Val Ser Lys Val Leu Val Asp
                725               730               735
His Phe Gly Tyr Thr Lys Asp Lys His Glu Gln Asp Met Val Asn
                740               745               750
Gly Ile Met Leu Ser Val Glu Lys Leu Ile Lys Asp Leu Lys Ser Lys
                755               760               765
Glu Val Pro Glu Ala Arg Ala Tyr Leu Arg Ile Leu Gly Glu Glu Leu
                770               775               780
Gly Phe Ala Ser Leu His Asp Leu Gln Leu Leu Gly Lys Leu Leu Leu
785               790               795               800
Met Gly Ala Arg Thr Leu Gln Gly Ile Pro Gln Met Ile Gly Glu Val
                    805               810               815
Ile Arg Lys Gly Ser Lys Asn Asp Phe Phe Leu His Tyr Ile Phe Met
                820               825               830
Glu Asn Ala Phe Glu Leu Pro Thr Gly Ala Gly Leu Gln Leu Gln Ile
                835               840               845
Ser Ser Ser Gly Val Ile Ala Pro Gly Ala Lys Ala Gly Val Lys Leu
                850               855               860
Glu Val Ala Asn Met Gln Ala Glu Leu Val Ala Lys Pro Ser Val Ser
865               870               875               880
Val Glu Phe Val Thr Asn Met Gly Ile Ile Ile Pro Asp Phe Ala Arg
                885               890               895
Ser Gly Val Gln Met Asn Thr Asn Phe Phe His Glu Ser Gly Leu Glu
                900               905               910
```

-continued

```
Ala His Val Ala Leu Lys Ala Gly Lys Leu Lys Phe Ile Ile Pro Ser
            915                 920                 925

Pro Lys Arg Pro Val Lys Leu Leu Ser Gly Gly Asn Thr Leu His Leu
930                 935                 940

Val Ser Thr Thr Lys Thr Glu Val Ile Pro Pro Leu Ile Glu Asn Arg
945                 950                 955                 960

Gln Ser Trp Ser Val Cys Lys Gln Val Phe Pro Gly Leu Asn Tyr Cys
                965                 970                 975

Thr Ser Gly Ala Tyr Ser Asn Ala Ser Ser Thr Asp Ser Ala Ser Tyr
            980                 985                 990

Tyr Pro Leu Thr Gly Asp Thr Arg Leu Glu Leu Glu Leu Arg Pro Thr
            995                1000                1005

Gly Glu Ile Glu Gln Tyr Ser Val Ser Ala Thr Tyr Glu Leu Gln
       1010                1015                1020

Arg Glu Asp Arg Ala Leu Val Asp Thr Leu Lys Phe Val Thr Gln
       1025                1030                1035

Ala Glu Gly Ala Lys Gln Thr Glu Ala Thr Met Thr Phe Lys Tyr
       1040                1045                1050

Asn Arg Gln Ser Met Thr Leu Ser Ser Glu Val Gln Ile Pro Asp
       1055                1060                1065

Phe Asp Val Asp Leu Gly Thr Ile Leu Arg Val Asn Asp Glu Ser
       1070                1075                1080

Thr Glu Gly Lys Thr Ser Tyr Arg Leu Thr Leu Asp Ile Gln Asn
       1085                1090                1095

Lys Lys Ile Thr Glu Val Ala Leu Met Gly His Leu Ser Cys Asp
       1100                1105                1110

Thr Lys Glu Glu Arg Lys Ile Lys Gly Val Ile Ser Ile Pro Arg
       1115                1120                1125

Leu Gln Ala Glu Ala Arg Ser Glu Ile Leu Ala His Trp Ser Pro
       1130                1135                1140

Ala Lys Leu Leu Leu Gln Met Asp Ser Ser Ala Thr Ala Tyr Gly
       1145                1150                1155

Ser Thr Val Ser Lys Arg Val Ala Trp His Tyr Asp Glu Glu Lys
       1160                1165                1170

Ile Glu Phe Glu Trp Asn Thr Gly Thr Asn Val Asp Thr Lys Lys
       1175                1180                1185

Met Thr Ser Asn Phe Pro Val Asp Leu Ser Asp Tyr Pro Lys Ser
       1190                1195                1200

Leu His Met Tyr Ala Asn Arg Leu Leu Asp His Arg Val Pro Gln
       1205                1210                1215

Thr Asp Met Thr Phe Arg His Val Gly Ser Lys Leu Ile Val Ala
       1220                1225                1230

Met Ser Ser Trp Leu Gln Lys Ala Ser Gly Ser Leu Pro Tyr Thr
       1235                1240                1245

Gln Thr Leu Gln Asp His Leu Asn Ser Leu Lys Glu Phe Asn Leu
       1250                1255                1260

Gln Asn Met Gly Leu Pro Asp Phe His Ile Pro Glu Asn Leu Phe
       1265                1270                1275

Leu Lys Ser Asp Gly Arg Val Lys Tyr Thr Leu Asn Lys Asn Ser
       1280                1285                1290

Leu Lys Ile Glu Ile Pro Leu Pro Phe Gly Gly Lys Ser Ser Arg
       1295                1300                1305
```

```
Asp Leu Lys Met Leu Glu Thr Val Arg Thr Pro Ala Leu His Phe
1310                1315                1320

Lys Ser Val Gly Phe His Leu Pro Ser Arg Glu Phe Gln Val Pro
1325                1330                1335

Thr Phe Thr Ile Pro Lys Leu Tyr Gln Leu Gln Val Pro Leu Leu
1340                1345                1350

Gly Val Leu Asp Leu Ser Thr Asn Val Tyr Ser Asn Leu Tyr Asn
1355                1360                1365

Trp Ser Ala Ser Tyr Ser Gly Gly Asn Thr Ser Thr Asp His Phe
1370                1375                1380

Ser Leu Arg Ala Arg Tyr His Met Lys Ala Asp Ser Val Val Asp
1385                1390                1395

Leu Leu Ser Tyr Asn Val Gln Gly Ser Gly Glu Thr Thr Tyr Asp
1400                1405                1410

His Lys Asn Thr Phe Thr Leu Ser Cys Asp Gly Ser Leu Arg His
1415                1420                1425

Lys Phe Leu Asp Ser Asn Ile Lys Phe Ser His Val Glu Lys Leu
1430                1435                1440

Gly Asn Asn Pro Val Ser Lys Gly Leu Leu Ile Phe Asp Ala Ser
1445                1450                1455

Ser Ser Trp Gly Pro Gln Met Ser Ala Ser Val His Leu Asp Ser
1460                1465                1470

Lys Lys Lys Gln His Leu Phe Val Lys Glu Val Lys Ile Asp Gly
1475                1480                1485

Gln Phe Arg Val Ser Ser Phe Tyr Ala Lys Gly Thr Tyr Gly Leu
1490                1495                1500

Ser Cys Gln Arg Asp Pro Asn Thr Gly Arg Leu Asn Gly Glu Ser
1505                1510                1515

Asn Leu Arg Phe Asn Ser Ser Tyr Leu Gln Gly Thr Asn Gln Ile
1520                1525                1530

Thr Gly Arg Tyr Glu Asp Gly Thr Leu Ser Leu Thr Ser Thr Ser
1535                1540                1545

Asp Leu Gln Ser Gly Ile Ile Lys Asn Thr Ala Ser Leu Lys Tyr
1550                1555                1560

Glu Asn Tyr Glu Leu Thr Leu Lys Ser Asp Thr Asn Gly Lys Tyr
1565                1570                1575

Lys Asn Phe Ala Thr Ser Asn Lys Met Asp Met Thr Phe Ser Lys
1580                1585                1590

Gln Asn Ala Leu Leu Arg Ser Glu Tyr Gln Ala Asp Tyr Glu Ser
1595                1600                1605

Leu Arg Phe Phe Ser Leu Leu Ser Gly Ser Leu Asn Ser His Gly
1610                1615                1620

Leu Glu Leu Asn Ala Asp Ile Leu Gly Thr Asp Lys Ile Asn Ser
1625                1630                1635

Gly Ala His Lys Ala Thr Leu Arg Ile Gly Gln Asp Gly Ile Ser
1640                1645                1650

Thr Ser Ala Thr Thr Asn Leu Lys Cys Ser Leu Leu Val Leu Glu
1655                1660                1665

Asn Glu Leu Asn Ala Glu Leu Gly Leu Ser Gly Ala Ser Met Lys
1670                1675                1680

Leu Thr Thr Asn Gly Arg Phe Arg Glu His Asn Ala Lys Phe Ser
1685                1690                1695

Leu Asp Gly Lys Ala Ala Leu Thr Glu Leu Ser Leu Gly Ser Ala
```

-continued

```
           1700                1705                1710

Tyr Gln Ala Met Ile Leu Gly Val Asp Ser Lys Asn Ile Phe Asn
           1715                1720                1725

Phe Lys Val Ser Gln Glu Gly Leu Lys Leu Ser Asn Asp Met Met
           1730                1735                1740

Gly Ser Tyr Ala Glu Met Lys Phe Asp His Thr Asn Ser Leu Asn
           1745                1750                1755

Ile Ala Gly Leu Ser Leu Asp Phe Ser Ser Lys Leu Asp Asn Ile
           1760                1765                1770

Tyr Ser Ser Asp Lys Phe Tyr Lys Gln Thr Val Asn Leu Gln Leu
           1775                1780                1785

Gln Pro Tyr Ser Leu Val Thr Thr Leu Asn Ser Asp Leu Lys Tyr
           1790                1795                1800

Asn Ala Leu Asp Leu Thr Asn Asn Gly Lys Leu Arg Leu Glu Pro
           1805                1810                1815

Leu Lys Leu His Val Ala Gly Asn Leu Lys Gly Ala Tyr Gln Asn
           1820                1825                1830

Asn Glu Ile Lys His Ile Tyr Ala Ile Ser Ser Ala Ala Leu Ser
           1835                1840                1845

Ala Ser Tyr Lys Ala Asp Thr Val Ala Lys Val Gln Gly Val Glu
           1850                1855                1860

Phe Ser His Arg Leu Asn Thr Asp Ile Ala Gly Leu Ala Ser Ala
           1865                1870                1875

Ile Asp Met Ser Thr Asn Tyr Asn Ser Asp Ser Leu His Phe Ser
           1880                1885                1890

Asn Val Phe Arg Ser Val Met Ala Pro Phe Thr Met Thr Ile Asp
           1895                1900                1905

Ala His Thr Asn Gly Asn Gly Lys Leu Ala Leu Trp Gly Glu His
           1910                1915                1920

Thr Gly Gln Leu Tyr Ser Lys Phe Leu Leu Lys Ala Glu Pro Leu
           1925                1930                1935

Ala Phe Thr Phe Ser His Asp Tyr Lys Gly Ser Thr Ser His His
           1940                1945                1950

Leu Val Ser Arg Lys Ser Ile Ser Ala Ala Leu Glu His Lys Val
           1955                1960                1965

Ser Ala Leu Leu Thr Pro Ala Glu Gln Thr Gly Thr Trp Lys Leu
           1970                1975                1980

Lys Thr Gln Phe Asn Asn Asn Glu Tyr Ser Gln Asp Leu Asp Ala
           1985                1990                1995

Tyr Asn Thr Lys Asp Lys Ile Gly Val Glu Leu Thr Gly Arg Thr
           2000                2005                2010

Leu Ala Asp Leu Thr Leu Leu Asp Ser Pro Ile Lys Val Pro Leu
           2015                2020                2025

Leu Leu Ser Glu Pro Ile Asn Ile Ile Asp Ala Leu Glu Met Arg
           2030                2035                2040

Asp Ala Val Glu Lys Pro Gln Glu Phe Thr Ile Val Ala Phe Val
           2045                2050                2055

Lys Tyr Asp Lys Asn Gln Asp Val His Ser Ile Asn Leu Pro Phe
           2060                2065                2070

Phe Glu Thr Leu Gln Glu Tyr Phe Glu Arg Asn Arg Gln Thr Ile
           2075                2080                2085

Ile Val Val Leu Glu Asn Val Gln Arg Asn Leu Lys His Ile Asn
           2090                2095                2100
```

-continued

```
Ile Asp Gln Phe Val Arg Lys Tyr Arg Ala Ala Leu Gly Lys Leu
2105             2110                 2115

Pro Gln Gln Ala Asn Asp Tyr Leu Asn Ser Phe Asn Trp Glu Arg
2120             2125                 2130

Gln Val Ser His Ala Lys Glu Lys Leu Thr Ala Leu Thr Lys Lys
2135             2140                 2145

Tyr Arg Ile Thr Glu Asn Asp Ile Gln Ile Ala Leu Asp Asp Ala
2150             2155                 2160

Lys Ile Asn Phe Asn Glu Lys Leu Ser Gln Leu Gln Thr Tyr Met
2165             2170                 2175

Ile Gln Phe Asp Gln Tyr Ile Lys Asp Ser Tyr Asp Leu His Asp
2180             2185                 2190

Leu Lys Ile Ala Ile Ala Asn Ile Ile Asp Glu Ile Ile Glu Lys
2195             2200                 2205

Leu Lys Ser Leu Asp Glu His Tyr His Ile Arg Val Asn Leu Val
2210             2215                 2220

Lys Thr Ile His Asp Leu His Leu Phe Ile Glu Asn Ile Asp Phe
2225             2230                 2235

Asn Lys Ser Gly Ser Ser Thr Ala Ser Trp Ile Gln Asn Val Asp
2240             2245                 2250

Thr Lys Tyr Gln Ile Arg Ile Gln Ile Gln Glu Lys Leu Gln Gln
2255             2260                 2265

Leu Lys Arg His Ile Gln Asn Ile Asp Ile Gln His Leu Ala Gly
2270             2275                 2280

Lys Leu Lys Gln His Ile Glu Ala Ile Asp Val Arg Val Leu Leu
2285             2290                 2295

Asp Gln Leu Gly Thr Thr Ile Ser Phe Glu Arg Ile Asn Asp Val
2300             2305                 2310

Leu Glu His Val Lys His Phe Val Ile Asn Leu Ile Gly Asp Phe
2315             2320                 2325

Glu Val Ala Glu Lys Ile Asn Ala Phe Arg Ala Lys Val His Glu
2330             2335                 2340

Leu Ile Glu Arg Tyr Glu Val Asp Gln Gln Ile Gln Val Leu Met
2345             2350                 2355

Asp Lys Leu Val Glu Leu Ala His Gln Tyr Lys Leu Lys Glu Thr
2360             2365                 2370

Ile Gln Lys Leu Ser Asn Val Leu Gln Gln Val Lys Ile Lys Asp
2375             2380                 2385

Tyr Phe Glu Lys Leu Val Gly Phe Ile Asp Asp Ala Val Lys Lys
2390             2395                 2400

Leu Asn Glu Leu Ser Phe Lys Thr Phe Ile Glu Asp Val Asn Lys
2405             2410                 2415

Phe Leu Asp Met Leu Ile Lys Lys Leu Lys Ser Phe Asp Tyr His
2420             2425                 2430

Gln Phe Val Asp Glu Thr Asn Asp Lys Ile Arg Glu Val Thr Gln
2435             2440                 2445

Arg Leu Asn Gly Glu Ile Gln Ala Leu Glu Leu Pro Gln Lys Ala
2450             2455                 2460

Glu Ala Leu Lys Leu Phe Leu Glu Glu Thr Lys Ala Thr Val Ala
2465             2470                 2475

Val Tyr Leu Glu Ser Leu Gln Asp Thr Lys Ile Thr Leu Ile Ile
2480             2485                 2490
```

-continued

```
Asn Trp Leu Gln Glu Ala Leu Ser Ser Ala Ser Leu Ala His Met
    2495                2500                2505

Lys Ala Lys Phe Arg Glu Thr Leu Glu Asp Thr Arg Asp Arg Met
    2510                2515                2520

Tyr Gln Met Asp Ile Gln Gln Glu Leu Gln Arg Tyr Leu Ser Leu
    2525                2530                2535

Val Gly Gln Val Tyr Ser Thr Leu Val Thr Tyr Ile Ser Asp Trp
    2540                2545                2550

Trp Thr Leu Ala Ala Lys Asn Leu Thr Asp Phe Ala Glu Gln Tyr
    2555                2560                2565

Ser Ile Gln Asp Trp Ala Lys Arg Met Lys Ala Leu Val Glu Gln
    2570                2575                2580

Gly Phe Thr Val Pro Glu Ile Lys Thr Ile Leu Gly Thr Met Pro
    2585                2590                2595

Ala Phe Glu Val Ser Leu Gln Ala Leu Gln Lys Ala Thr Phe Gln
    2600                2605                2610

Thr Pro Asp Phe Ile Val Pro Leu Thr Asp Leu Arg Ile Pro Ser
    2615                2620                2625

Val Gln Ile Asn Phe Lys Asp Leu Lys Asn Ile Lys Ile Pro Ser
    2630                2635                2640

Arg Phe Ser Thr Pro Glu Phe Thr Ile Leu Asn Thr Phe His Ile
    2645                2650                2655

Pro Ser Phe Thr Ile Asp Phe Val Glu Met Lys Val Lys Ile Ile
    2660                2665                2670

Arg Thr Ile Asp Gln Met Leu Asn Ser Glu Leu Gln Trp Pro Val
    2675                2680                2685

Pro Asp Ile Tyr Leu Arg Asp Leu Lys Val Glu Asp Ile Pro Leu
    2690                2695                2700

Ala Arg Ile Thr Leu Pro Asp Phe Arg Leu Pro Glu Ile Ala Ile
    2705                2710                2715

Pro Glu Phe Ile Ile Pro Thr Leu Asn Leu Asn Asp Phe Gln Val
    2720                2725                2730

Pro Asp Leu His Ile Pro Glu Phe Gln Leu Pro His Ile Ser His
    2735                2740                2745

Thr Ile Glu Val Pro Thr Phe Gly Lys Leu Tyr Ser Ile Leu Lys
    2750                2755                2760

Ile Gln Ser Pro Leu Phe Thr Leu Asp Ala Asn Ala Asp Ile Gly
    2765                2770                2775

Asn Gly Thr Thr Ser Ala Asn Glu Ala Gly Ile Ala Ala Ser Ile
    2780                2785                2790

Thr Ala Lys Gly Glu Ser Lys Leu Glu Val Leu Asn Phe Asp Phe
    2795                2800                2805

Gln Ala Asn Ala Gln Leu Ser Asn Pro Lys Ile Asn Pro Leu Ala
    2810                2815                2820

Leu Lys Glu Ser Val Lys Phe Ser Ser Lys Tyr Leu Arg Thr Glu
    2825                2830                2835

His Gly Ser Glu Met Leu Phe Phe Gly Asn Ala Ile Glu Gly Lys
    2840                2845                2850

Ser Asn Thr Val Ala Ser Leu His Thr Glu Lys Asn Thr Leu Glu
    2855                2860                2865

Leu Ser Asn Gly Val Ile Val Lys Ile Asn Asn Gln Leu Thr Leu
    2870                2875                2880

Asp Ser Asn Thr Lys Tyr Phe His Lys Leu Asn Ile Pro Lys Leu
```

```
                2885                2890                2895
Asp Phe Ser Ser Gln Ala Asp Leu Arg Asn Glu Ile Lys Thr Leu
    2900                2905                2910

Leu Lys Ala Gly His Ile Ala Trp Thr Ser Ser Gly Lys Gly Ser
    2915                2920                2925

Trp Lys Trp Ala Cys Pro Arg Phe Ser Asp Glu Gly Thr His Glu
    2930                2935                2940

Ser Gln Ile Ser Phe Thr Ile Glu Gly Pro Leu Thr Ser Phe Gly
    2945                2950                2955

Leu Ser Asn Lys Ile Asn Ser Lys His Leu Arg Val Asn Gln Asn
    2960                2965                2970

Leu Val Tyr Glu Ser Gly Ser Leu Asn Phe Ser Lys Leu Glu Ile
    2975                2980                2985

Gln Ser Gln Val Asp Ser Gln His Val Gly His Ser Val Leu Thr
    2990                2995                3000

Ala Lys Gly Met Ala Leu Phe Gly Glu Gly Lys Ala Glu Phe Thr
    3005                3010                3015

Gly Arg His Asp Ala His Leu Asn Gly Lys Val Ile Gly Thr Leu
    3020                3025                3030

Lys Asn Ser Leu Phe Phe Ser Ala Gln Pro Phe Glu Ile Thr Ala
    3035                3040                3045

Ser Thr Asn Asn Glu Gly Asn Leu Lys Val Arg Phe Pro Leu Arg
    3050                3055                3060

Leu Thr Gly Lys Ile Asp Phe Leu Asn Asn Tyr Ala Leu Phe Leu
    3065                3070                3075

Ser Pro Ser Ala Gln Gln Ala Ser Trp Gln Val Ser Ala Arg Phe
    3080                3085                3090

Asn Gln Tyr Lys Tyr Asn Gln Asn Phe Ser Ala Gly Asn Asn Glu
    3095                3100                3105

Asn Ile Met Glu Ala His Val Gly Ile Asn Gly Glu Ala Asn Leu
    3110                3115                3120

Asp Phe Leu Asn Ile Pro Leu Thr Ile Pro Glu Met Arg Leu Pro
    3125                3130                3135

Tyr Thr Ile Ile Thr Thr Pro Pro Leu Lys Asp Phe Ser Leu Trp
    3140                3145                3150

Glu Lys Thr Gly Leu Lys Glu Phe Leu Lys Thr Thr Lys Gln Ser
    3155                3160                3165

Phe Asp Leu Ser Val Lys Ala Gln Tyr Lys Lys Asn Lys His Arg
    3170                3175                3180

His Ser Ile Thr Asn Pro Leu Ala Val Leu Cys Glu Phe Ile Ser
    3185                3190                3195

Gln Ser Ile Lys Ser Phe Asp Arg His Phe Glu Lys Asn Arg Asn
    3200                3205                3210

Asn Ala Leu Asp Phe Val Thr Lys Ser Tyr Asn Glu Thr Lys Ile
    3215                3220                3225

Lys Phe Asp Lys Tyr Lys Ala Glu Lys Ser His Asp Glu Leu Pro
    3230                3235                3240

Arg Thr Phe Gln Ile Pro Gly Tyr Thr Val Pro Val Val Asn Val
    3245                3250                3255

Glu Val Ser Pro Phe Thr Ile Glu Met Ser Ala Phe Gly Tyr Val
    3260                3265                3270

Phe Pro Lys Ala Val Ser Met Pro Ser Phe Ser Ile Leu Gly Ser
    3275                3280                3285
```

```
Asp Val Arg Val Pro Ser Tyr Thr Leu Ile Leu Pro Ser Leu Glu
3290            3295            3300

Leu Pro Val Leu His Val Pro Arg Asn Leu Lys Leu Ser Leu Pro
3305            3310            3315

Asp Phe Lys Glu Leu Cys Thr Ile Ser His Ile Phe Ile Pro Ala
3320            3325            3330

Met Gly Asn Ile Thr Tyr Asp Phe Ser Phe Lys Ser Ser Val Ile
3335            3340            3345

Thr Leu Asn Thr Asn Ala Glu Leu Phe Asn Gln Ser Asp Ile Val
3350            3355            3360

Ala His Leu Leu Ser Ser Ser Ser Val Ile Asp Ala Leu Gln
3365            3370            3375

Tyr Lys Leu Glu Gly Thr Thr Arg Leu Thr Arg Lys Arg Gly Leu
3380            3385            3390

Lys Leu Ala Thr Ala Leu Ser Leu Ser Asn Lys Phe Val Glu Gly
3395            3400            3405

Ser His Asn Ser Thr Val Ser Leu Thr Thr Lys Asn Met Glu Val
3410            3415            3420

Ser Val Ala Thr Thr Thr Lys Ala Gln Ile Pro Ile Leu Arg Met
3425            3430            3435

Asn Phe Lys Gln Glu Leu Asn Gly Asn Thr Lys Ser Lys Pro Thr
3440            3445            3450

Val Ser Ser Ser Met Glu Phe Lys Tyr Asp Phe Asn Ser Ser Met
3455            3460            3465

Leu Tyr Ser Thr Ala Lys Gly Ala Val Asp His Lys Leu Ser Leu
3470            3475            3480

Glu Ser Leu Thr Ser Tyr Phe Ser Ile Glu Ser Ser Thr Lys Gly
3485            3490            3495

Asp Val Lys Gly Ser Val Leu Ser Arg Glu Tyr Ser Gly Thr Ile
3500            3505            3510

Ala Ser Glu Ala Asn Thr Tyr Leu Asn Ser Lys Ser Thr Arg Ser
3515            3520            3525

Ser Val Lys Leu Gln Gly Thr Ser Lys Ile Asp Asp Ile Trp Asn
3530            3535            3540

Leu Glu Val Lys Glu Asn Phe Ala Gly Glu Ala Thr Leu Gln Arg
3545            3550            3555

Ile Tyr Ser Leu Trp Glu His Ser Thr Lys Asn His Leu Gln Leu
3560            3565            3570

Glu Gly Leu Phe Phe Thr Asn Gly Glu His Thr Ser Lys Ala Thr
3575            3580            3585

Leu Glu Leu Ser Pro Trp Gln Met Ser Ala Leu Val Gln Val His
3590            3595            3600

Ala Ser Gln Pro Ser Ser Phe His Asp Phe Pro Asp Leu Gly Gln
3605            3610            3615

Glu Val Ala Leu Asn Ala Asn Thr Lys Asn Gln Lys Ile Arg Trp
3620            3625            3630

Lys Asn Glu Val Arg Ile His Ser Gly Ser Phe Gln Ser Gln Val
3635            3640            3645

Glu Leu Ser Asn Asp Gln Glu Lys Ala His Leu Asp Ile Ala Gly
3650            3655            3660

Ser Leu Glu Gly His Leu Arg Phe Leu Lys Asn Ile Ile Leu Pro
3665            3670            3675
```

-continued

Val Tyr Asp Lys Ser Leu Trp Asp Phe Leu Lys Leu Asp Val Thr
3680                    3685                3690

Thr Ser Ile Gly Arg Arg Gln His Leu Arg Val Ser Thr Ala Phe
3695                    3700                3705

Val Tyr Thr Lys Asn Pro Asn Gly Tyr Ser Phe Ser Ile Pro Val
3710                    3715                3720

Lys Val Leu Ala Asp Lys Phe Ile Ile Pro Gly Leu Lys Leu Asn
3725                    3730                3735

Asp Leu Asn Ser Val Leu Val Met Pro Thr Phe His Val Pro Phe
3740                    3745                3750

Thr Asp Leu Gln Val Pro Ser Cys Lys Leu Asp Phe Arg Glu Ile
3755                    3760                3765

Gln Ile Tyr Lys Lys Leu Arg Thr Ser Ser Phe Ala Leu Asn Leu
3770                    3775                3780

Pro Thr Leu Pro Glu Val Lys Phe Pro Glu Val Asp Val Leu Thr
3785                    3790                3795

Lys Tyr Ser Gln Pro Glu Asp Ser Leu Ile Pro Phe Phe Glu Ile
3800                    3805                3810

Thr Val Pro Glu Ser Gln Leu Thr Val Ser Gln Phe Thr Leu Pro
3815                    3820                3825

Lys Ser Val Ser Asp Gly Ile Ala Ala Leu Asp Leu Asn Ala Val
3830                    3835                3840

Ala Asn Lys Ile Ala Asp Phe Glu Leu Pro Thr Ile Ile Val Pro
3845                    3850                3855

Glu Gln Thr Ile Glu Ile Pro Ser Ile Lys Phe Ser Val Pro Ala
3860                    3865                3870

Gly Ile Val Ile Pro Ser Phe Gln Ala Leu Thr Ala Arg Phe Glu
3875                    3880                3885

Val Asp Ser Pro Val Tyr Asn Ala Thr Trp Ser Ala Ser Leu Lys
3890                    3895                3900

Asn Lys Ala Asp Tyr Val Glu Thr Val Leu Asp Ser Thr Cys Ser
3905                    3910                3915

Ser Thr Val Gln Phe Leu Glu Tyr Glu Leu Asn Val Leu Gly Thr
3920                    3925                3930

His Lys Ile Glu Asp Gly Thr Leu Ala Ser Lys Thr Lys Gly Thr
3935                    3940                3945

Phe Ala His Arg Asp Phe Ser Ala Glu Tyr Glu Glu Asp Gly Lys
3950                    3955                3960

Tyr Glu Gly Leu Gln Glu Trp Glu Gly Lys Ala His Leu Asn Ile
3965                    3970                3975

Lys Ser Pro Ala Phe Thr Asp Leu His Leu Arg Tyr Gln Lys Asp
3980                    3985                3990

Lys Lys Gly Ile Ser Thr Ser Ala Ala Ser Pro Ala Val Gly Thr
3995                    4000                4005

Val Gly Met Asp Met Asp Glu Asp Asp Asp Phe Ser Lys Trp Asn
4010                    4015                4020

Phe Tyr Tyr Ser Pro Gln Ser Ser Pro Asp Lys Lys Leu Thr Ile
4025                    4030                4035

Phe Lys Thr Glu Leu Arg Val Arg Glu Ser Asp Glu Glu Thr Gln
4040                    4045                4050

Ile Lys Val Asn Trp Glu Glu Glu Ala Ala Ser Gly Leu Leu Thr
4055                    4060                4065

Ser Leu Lys Asp Asn Val Pro Lys Ala Thr Gly Val Leu Tyr Asp

-continued

```
            4070            4075            4080
Tyr Val Asn Lys Tyr His Trp Glu His Thr Gly Leu Thr Leu Arg
            4085            4090            4095
Glu Val Ser Ser Lys Leu Arg Arg Asn Leu Gln Asn Asn Ala Glu
            4100            4105            4110
Trp Val Tyr Gln Gly Ala Ile Arg Gln Ile Asp Asp Ile Asp Val
            4115            4120            4125
Arg Phe Gln Lys Ala Ala Ser Gly Thr Thr Gly Thr Tyr Gln Glu
            4130            4135            4140
Trp Lys Asp Lys Ala Gln Asn Leu Tyr Gln Glu Leu Leu Thr Gln
            4145            4150            4155
Glu Gly Gln Ala Ser Phe Gln Gly Leu Lys Asp Asn Val Phe Asp
            4160            4165            4170
Gly Leu Val Arg Val Thr Gln Glu Phe His Met Lys Val Lys His
            4175            4180            4185
Leu Ile Asp Ser Leu Ile Asp Phe Leu Asn Phe Pro Arg Phe Gln
            4190            4195            4200
Phe Pro Gly Lys Pro Gly Ile Tyr Thr Arg Glu Glu Leu Cys Thr
            4205            4210            4215
Met Phe Ile Arg Glu Val Gly Thr Val Leu Ser Gln Val Tyr Ser
            4220            4225            4230
Lys Val His Asn Gly Ser Glu Ile Leu Phe Ser Tyr Phe Gln Asp
            4235            4240            4245
Leu Val Ile Thr Leu Pro Phe Glu Leu Arg Lys His Lys Leu Ile
            4250            4255            4260
Asp Val Ile Ser Met Tyr Arg Glu Leu Leu Lys Asp Leu Ser Lys
            4265            4270            4275
Glu Ala Gln Glu Val Phe Lys Ala Ile Gln Ser Leu Lys Thr Thr
            4280            4285            4290
Glu Val Leu Arg Asn Leu Gln Asp Leu Leu Gln Phe Ile Phe Gln
            4295            4300            4305
Leu Ile Glu Asp Asn Ile Lys Gln Leu Lys Glu Met Lys Phe Thr
            4310            4315            4320
Tyr Leu Ile Asn Tyr Ile Gln Asp Glu Ile Asn Thr Ile Phe Ser
            4325            4330            4335
Asp Tyr Ile Pro Tyr Val Phe Lys Leu Leu Lys Glu Asn Leu Cys
            4340            4345            4350
Leu Asn Leu His Lys Phe Asn Glu Phe Ile Gln Asn Glu Leu Gln
            4355            4360            4365
Glu Ala Ser Gln Glu Leu Gln Gln Ile His Gln Tyr Ile Met Ala
            4370            4375            4380
Leu Arg Glu Glu Tyr Phe Asp Pro Ser Ile Val Gly Trp Thr Val
            4385            4390            4395
Lys Tyr Tyr Glu Leu Glu Glu Lys Ile Val Ser Leu Ile Lys Asn
            4400            4405            4410
Leu Leu Val Ala Leu Lys Asp Phe His Ser Glu Tyr Ile Val Ser
            4415            4420            4425
Ala Ser Asn Phe Thr Ser Gln Leu Ser Ser Gln Val Glu Gln Phe
            4430            4435            4440
Leu His Arg Asn Ile Gln Glu Tyr Leu Ser Ile Leu Thr Asp Pro
            4445            4450            4455
Asp Gly Lys Gly Lys Glu Lys Ile Ala Glu Leu Ser Ala Thr Ala
            4460            4465            4470
```

```
Gln Glu Ile Ile Lys Ser Gln Ala Ile Ala Thr Lys Lys Ile Ile
    4475                4480                4485

Ser Asp Tyr His Gln Gln Phe Arg Tyr Lys Leu Gln Asp Phe Ser
    4490                4495                4500

Asp Gln Leu Ser Asp Tyr Tyr Glu Lys Phe Ile Ala Glu Ser Lys
    4505                4510                4515

Arg Leu Ile Asp Leu Ser Ile Gln Asn Tyr His Thr Phe Leu Ile
    4520                4525                4530

Tyr Ile Thr Glu Leu Leu Lys Lys Leu Gln Ser Thr Thr Val Met
    4535                4540                4545

Asn Pro Tyr Met Lys Leu Ala Pro Gly Glu Leu Thr Ile Ile Leu
    4550                4555                4560

<210> SEQ ID NO 2
<211> LENGTH: 482
<212> TYPE: PRT
<213> ORGANISM: Homo sapiens

<400> SEQUENCE: 2

Met Ser Ile Arg Val Thr Gln Lys Ser Tyr Lys Val Ser Thr Ser Gly
1               5                   10                  15

Pro Arg Ala Phe Ser Ser Arg Ser Tyr Thr Ser Gly Pro Gly Ser Arg
                20                  25                  30

Ile Ser Ser Ser Ser Phe Ser Arg Val Gly Ser Ser Asn Phe Arg Gly
                35                  40                  45

Gly Leu Gly Gly Gly Tyr Gly Gly Ala Ser Gly Met Gly Gly Ile Thr
        50                  55                  60

Ala Val Thr Val Asn Gln Ser Leu Leu Ser Pro Leu Val Leu Glu Val
65                  70                  75                  80

Asp Pro Asn Ile Gln Ala Val Arg Thr Gln Glu Lys Glu Gln Ile Lys
                85                  90                  95

Thr Leu Asn Asn Lys Phe Ala Ser Phe Ile Asp Lys Val Arg Phe Leu
                100                 105                 110

Glu Gln Gln Asn Lys Met Leu Glu Thr Lys Trp Ser Leu Leu Gln Gln
                115                 120                 125

Gln Lys Thr Ala Arg Ser Asn Met Asp Asn Met Phe Glu Ser Tyr Ile
                130                 135                 140

Asn Asn Leu Arg Arg Gln Leu Glu Thr Leu Gly Gln Glu Lys Leu Lys
145                 150                 155                 160

Leu Glu Ala Glu Leu Gly Asn Met Gln Gly Leu Val Glu Asp Phe Lys
                165                 170                 175

Asn Lys Tyr Glu Asp Glu Ile Asn Lys Arg Thr Glu Met Glu Asn Glu
                180                 185                 190

Phe Val Leu Ile Lys Lys Asp Val Asp Glu Ala Tyr Met Asn Lys Val
                195                 200                 205

Glu Leu Glu Ser Arg Leu Glu Gly Leu Thr Asp Glu Ile Asn Phe Leu
                210                 215                 220

Arg Gln Leu Tyr Glu Glu Glu Ile Arg Glu Leu Gln Ser Gln Ile Ser
225                 230                 235                 240

Asp Thr Ser Val Val Leu Ser Met Asp Asn Ser Arg Ser Leu Asp Met
                245                 250                 255

Asp Ser Ile Ile Ala Glu Val Lys Ala Gln Tyr Glu Asp Ile Ala Asn
                260                 265                 270

Arg Ser Arg Ala Glu Ala Glu Ser Met Tyr Gln Ile Lys Tyr Glu Glu
```

```
                275                 280                 285
Leu Gln Ser Leu Ala Gly Lys His Gly Asp Asp Leu Arg Arg Thr Lys
            290                 295                 300
Thr Glu Ile Ser Glu Met Asn Arg Asn Ile Ser Arg Leu Gln Ala Glu
305                 310                 315                 320
Ile Glu Gly Leu Lys Gly Gln Arg Ala Ser Leu Glu Ala Ala Ile Ala
                325                 330                 335
Asp Ala Glu Gln Arg Gly Glu Leu Ala Ile Lys Asp Ala Asn Ala Lys
            340                 345                 350
Leu Ser Glu Leu Glu Ala Ala Leu Gln Arg Ala Lys Gln Asp Met Ala
            355                 360                 365
Arg Gln Leu Arg Glu Tyr Gln Glu Leu Met Asn Val Lys Leu Ala Leu
        370                 375                 380
Asp Ile Glu Ile Ala Thr Tyr Arg Lys Leu Leu Glu Gly Glu Glu Ser
385                 390                 395                 400
Arg Leu Glu Ser Gly Met Gln Asn Met Ser Ile His Thr Lys Thr Thr
                405                 410                 415
Gly Gly Tyr Ala Gly Gly Leu Ser Ser Ala Tyr Gly Gly Ser Gln Ala
                420                 425                 430
Gly Leu Ser Tyr Ser Leu Gly Ser Ser Phe Gly Ser Gly Ala Gly Ser
            435                 440                 445
Ser Ser Phe Ser Arg Thr Ser Ser Ser Arg Ala Val Val Val Lys Lys
        450                 455                 460
Ile Glu Thr Arg Asp Gly Lys Leu Val Ser Glu Ser Ser Asp Val Leu
465                 470                 475                 480
Pro Lys
```

ULTRA-SMALL APOB-CONTAINING PARTICLES AND METHODS OF USE THEREOF

CROSS-REFERENCE

This application claims the benefit of U.S. Provisional Patent Application No. 61/497,847, filed Jun. 16, 2011, which application is incorporated herein by reference in its entirety.

BACKGROUND

Lipoproteins function to transport lipids around the body. Lipids are generally hydrophobic, while the extracellular environment is generally aqueous. Apolipoproteins bind to lipids, such as cholesterol and triglycerides, and facilitate their transport through the aqueous environment. Apolipoprotein B (apoB) represents most of the protein content in low density lipoprotein (LDL), and is also present in intermediate-density lipoproteins (IDL) and very low density lipoproteins (VLDL). Apolipoprotein AI (apoAI) is the principal protein in high density lipoprotein (HDL) and represents about 70%.

The total cholesterol/HDL cholesterol ratio and the LDL/HDL cholesterol ratio are two indicators of vascular disease risk, including cardiovascular disease (CVD) risk. For example, an increase in the total cholesterol concentration, and specifically LDL cholesterol, is an atherogenic lipid marker. Reduced HDL cholesterol concentration is associated with various risk factors, including components of the metabolic syndrome.

LITERATURE

Millán et al. (2009) *Vascular Health and Risk Management* 5:757; Superko and Gadesam (2008) *Curr. Atheroscler. Rep.* 10:377; U.S. Pat. No. 7,781,219; U.S. Patent Publication No. 20100183607; U.S. Patent Publication No. 20100179066; U.S. Patent Publication No. 20090155915; WO 2010/115200; WO 2010/115094.

SUMMARY

The present disclosure describes a very high density, ultra small lipid depleted apolipoprotein B containing particle that may be indicative of increased cardiovascular disease risk. These particles may contain other proteins, such as cytokeratins. The isolated particles are useful in diagnostic assays, which are also provided.

BRIEF DESCRIPTION OF THE DRAWINGS

FIGS. 17A-D depicts an amino acid sequence of apoB-100.

FIG. 18 depicts an amino acid sequence of cytokeratin 8.

DEFINITIONS

Figure 1:
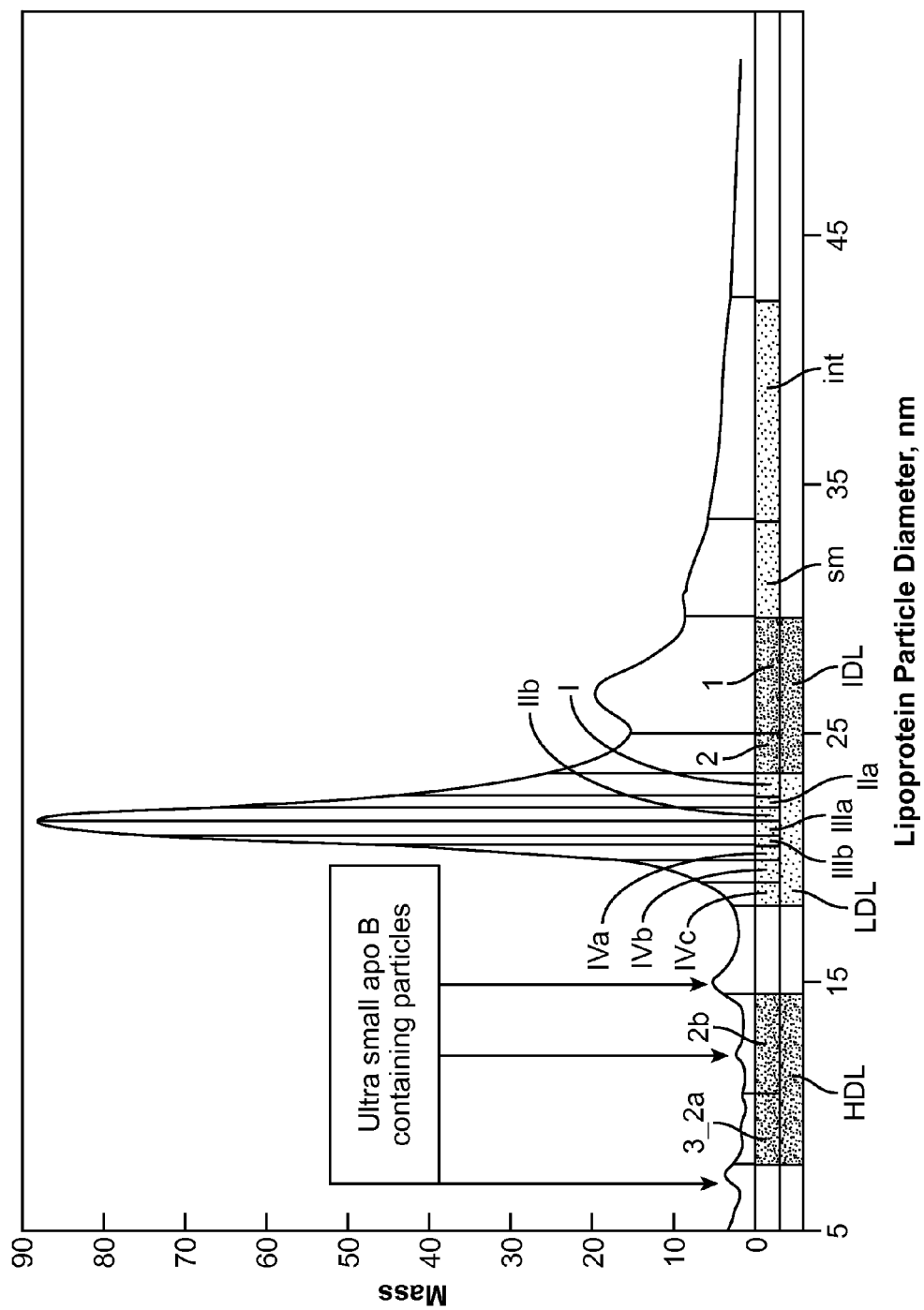
FIG. 1 depicts the ion mobility (IM) analysis of particles isolated from plasma from a representative individual using a specific anti-apoB antibody conjugated to magnetic beads.

As used herein, the terms "determining," "measuring," and "assessing," and "assaying" are used interchangeably and include both quantitative and qualitative determinations.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially pure" refers to a compound that is removed from its natural environment and is at least 80% free, at least 85% free, at least 90%, at least 95%, at least 98%, or at least 99%, free from other components with which it is naturally associated.

"Predisposition" as used herein is substantially synonymous with risk, inclination, tendency, predilection, or susceptibility.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc. In some cases, the term refers to a human.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an apoB particle" includes a plurality of such particles and reference to "the diagnostic assay" includes reference to one or more diagnostic assays and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure describes a species of very high density, ultra small, lipid-depleted apolipoprotein B containing particles. These particles may contain other proteins including cytokeratins. The isolated particles are useful in diagnostic assays, which are also provided.

Apolipoprotein Particle

The present disclosure provides an isolated particle comprising: a) apolipoprotein B (apoB); and b) a cytokeratin-8 polypeptide having a molecular weight of about 52 kDa. A subject isolated particle is referred to herein as a "very high density, ultra small, de-lipidated apolipoprotein B containing particle". A subject "very high density, ultra small, de-lipidated apolipoprotein B containing particle" is characterized by having an average particle diameter in the range of from about 7.1 nm to about 22 nm; having a density greater than 1.21 g/mL; and having undetectable content of cholesterol and triglycerides by sensitive assays.

A subject "very high density, ultra small, de-lipidated apolipoprotein B containing particle" can have an average particle diameter in the range of from approximately 7.1 nm to 22 nm, e.g., from about 7.1 nm to about 15 nm, from about 15 nm to about 18 nm, or from about 18 nm to about 22 nm. Thus, e.g., at least about 80%, at least about 85%, at least about 90%, at least about 95%, at least about 98%, or at least about 99%, of the particles in a population of "very high density, ultra small, de-lipidated apolipoprotein B containing particles" has an average particle diameter in a range of from about 7.1 nm to about 15 nm, from about 15 nm to about 18 nm, or from about 18 nm to about 22 nm.

A subject "very high density, ultra small, de-lipidated apolipoprotein B containing particle" can have a size in the range of from about 71 Å to about 220 Å, e.g., from about 71 Å to about 160 Å, from about 160 Å to about 175 Å, from about 175 Å to about 200 Å, from about 200 Å to about 210 Å, from about 210 Å to about 220 Å.

A subject "very high density, ultra small, de-lipidated apolipoprotein B containing particle" generally has a density greater than 1.21 g/mL, e.g., a subject "very high density, ultra small, de-lipidated apolipoprotein B containing particle" generally has a density of from about 1.21 g/mL to about 1.3 g/mL, or from about 1.3 g/mL to about 1.35 g/mL. Thus, e.g., at least about 80%, at least about 85%, at least about 90%, at least about 95%, at least about 98%, or at least about 99%, of the particles in a population of "very high density, ultra small de-lipidated apolipoprotein B containing particles" has a density of from about 1.21 g/mL to about 1.3 g/mL, or from about 1.3 g/mL to about 1.35 g/mL.

An isolated "very high density, ultra small, de-lipidated apolipoprotein B containing particle" of the present disclosure has substantially no lipid. For example, a subject "very high density, ultra small, de-lipidated apolipoprotein B containing particle" has substantially no cholesterol, e.g., a subject "very high density, ultra small, de-lipidated apolipoprotein B containing particle" will have less than about 10%, less than about 5%, less than about 3%, less than about 2%, less than about 1%, less than about 0.5%, less than about 0.2%, less than about 0.1%, or less than about 0.01%, by weight, cholesterol. In some cases, a subject "very high density, ultra small, de-lipidated apolipoprotein B containing particle" has no detectable cholesterol.

As another example, a subject "very high density, ultra small, de-lipidated apolipoprotein B containing particle" has substantially no triglycerides, e.g., a subject "very high density, ultra small, de-lipidated apolipoprotein B containing particle" will have less than about 10%, less than about 5%, less than about 3%, less than about 2%, less than about 1%, less than about 0.5%, less than about 0.2%, less than about 0.1%, or less than about 0.01%, by weight, triglycerides. In some cases, a subject "very high density, ultra small, de-lipidated apolipoprotein B containing particle" has no detectable triglycerides.

Apolipoprotein-B 100

Amino acid sequences of apoB-100 polypeptides are known in the art. For example, the following GenBank accession numbers provide amino acid sequences of apoB-100 polypeptides; 1) GenBank Accession No. NP_000375.2 (*Homo sapiens* apoB-100); 2) GenBank Accession No. XP_515323.2 (*Pan troglodytes* apoB-100); 3) GenBank Accession No. XP_001097500.1 (*Macaca mulatta* apoB-100); 4) GenBank Accession No. XP_001501729.1 (*Equus caballus* apoB-100); 5) GenBank Accession No. NP_033823.2 (*Mus musculus* apoB-100); and 6) GenBank Accession No. NP_062160.2 (*Rattus norvegicus* apoB-100).

In some embodiments, an apoB-100 polypeptide that is included in a subject "very high density, ultra small de-lipidated apolipoprotein B containing particle" comprises an amino acid sequence having at least about 85%, at least about 90%, at least about 95%, at least about 98%, at least about 99%, or 100%, amino acid sequence identity with amino acids 28-4563 of the amino acid sequence set forth in FIGS. 17A-D and SEQ ID NO:1.

Cytokeratin 8

Amino acid sequences of cytokeratin 8 polypeptides are known in the art. For example, the following GenBank accession numbers provide amino acid sequences of cytokeratin-8 polypeptides: 1) GenBank Accession No. AAA35763 (*Homo sapiens* cytokeratin 8); 2) GenBank Accession No. AAA19668.1 (*Rattus norvegicus* cytokeratin 8); 3) GenBank Accession No. AAI06155.1 (*Mus musculus* cytokeratin 8); 4) GenBank Accession No. AAI54778.1 (*Danio rerio* cytokeratin 8); and 5) GenBank Accession No. XP_002742819 (*Callithrix jacchus* cytokeratin 8).

In some embodiments, a cytokeratin-8 polypeptide that is included in a subject "very high density, ultra small, lipid depleted apolipoprotein B containing particle" comprises an amino acid sequence having at least about 85%, at least about 90%, at least about 95%, at least about 98%, at least about 99%, or 100%, amino acid sequence identity with the amino acid sequence set forth in FIG. 18 and SEQ ID NO:2.

Methods of Isolating a Very High Density, Ultra Small, Lipid Depleted Apolipoprotein B Containing Particle The present disclosure provides a number of methods to isolate the ultra-small apo B containing particles which may contain cytokeratin 8. An immunoaffinity method can be used. For example anti-apoB antibody that is immobilized (e.g., on a column, a magnetic bead, and the like) can be contacted with a sample (e.g., plasma, such as human plasma) containing the particle, where the particle binds to the immobilized anti-apoB antibody, forming an immobilized anti-apoB-particle complex. The particle in the immobilized complex can be eluted.

For example, Apo B antibody (antibody specific for apoB) was conjugated to the Dynabeads® M-280 Tosylactivated using manufacturer recommended procedure with slight modification such as replacing the bovine serum albumin (BSA) in buffer D with non-fat dry milk, replacing BSA in buffer E with Tween 20 and antibody conjugation temperature from 37° C. for 12-18 hours to 22-25° C. (room temperature) for 24 hours. Serum sample was diluted 1:200 in buffer D and incubated with apo B-specific monoclonal antibody conjugated to magnetic Dynabeads at 25° C. with continuous rocking/mixing for 30 minutes. At the end of the incubation period, the magnetic field was applied to the tubes, then supernatant was removed followed by 3 wash with phosphate buffer saline (PBS). Glycine buffer (pH 2.8) was used to elute/release the apo B particles from their respected antibody. Then the pH was immediately adjusted to around 7.5 with 2-2.5 µL of the 2.5 mmol NaOH. The eluted particles were dialyzed over night against 25 mmol ammonium acetate before analysis with ion mobility (IM), see FIG. 1. Furthermore, the eluted particles were assayed using an enzyme-linked immunosorbent assay (ELISA) to estimate the recovery of this method.

Figure 2:
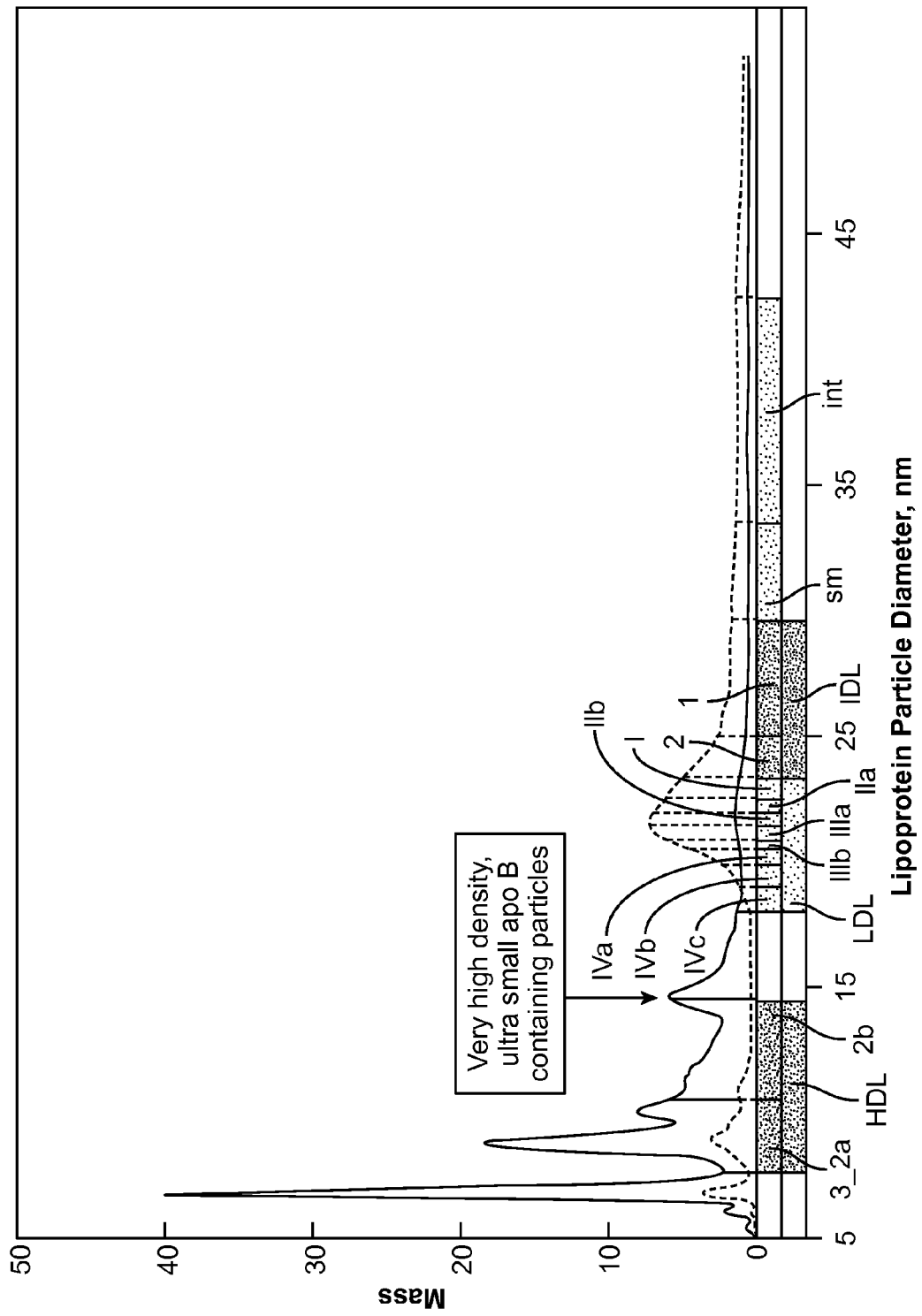
FIG. 2 depicts ion mobility analysis of the d<1.21 g/ml ultracentrifugal fraction of plasma (blue) and the d>1.21 g/ml ultracentrifugal fraction of plasma (black) from a representative individual.

The density gradient is one of the methods used. The density of the plasma was adjusted to 1.21 g/mL (by adding 1.91 gram NaBr to 6.503 mL plasma) and to 1.25 g/L (by adding 2.294 gram NaBr to 6.4 mL plasma). After completely dissolving the NaBr into the plasma, 6 mL was taken and added to the ultracentrifuge tubes, and then 6 µL 10 mmol trolox (6-hydroxy-2,5,7,8-tetramethylchroman-2-carboxylic acid) was added to each tube to prevent oxidation of lipoproteins. Ultracentrifugation was carried out at 40,000 rpm (115,046 g force) and 15° C. for 24 hours. At the end of the ultracentrifugation, the tubes were carefully removed and the top 1.5 mL was harvested from the all tubes. The top and bottom fractions were dialyzed against 25 mmol ammonium acetate for approximately 24 hours at 4° C. Following the dialysis of the plasma fractions, Ion Mobility was used to measure particles size (FIG. 2). Also the top and bottom density fractions were subject to above described immunoassay isolation procedure to isolate the very high density ultra-small dense apo B containing particles (see FIG. 3). In addition, the concentration of apo B was measured by ELISA assay using monoclonal specific antibody (see, e.g., Table 1, below, for apo B ultracentrifugation recovery by ELISA).

The present disclosure also provides a gradient gel electrophoresis method of isolating a very high density, ultra small apolipoprotein B containing particle described above. A subject method generally involves applying a sample (e.g., a plasma sample) comprising the very high density, ultra small apolipoprotein B containing particles as described above, on a 2-14% non-denaturing gradient polyacrylamide gel; separating the components of the sample on the gel by applying increasing voltage to the gel; and collecting fractions that advance beyond an LDL-IV standard band in the gel.

Pre-stained lipoprotein standards can be run alongside the sample, to provide an indication as to where to elute the sample. Suitable standards include: Lp(a); Large LDL; LDL-III; and LDL-IV. "Lp(a)" refers to biological particles consisting of LDL covalently attached to the protein lipoprotein A.

For example, a plasma (e.g., human plasma) sample is applied to a slot in a 2-14% non-denaturing gradient polyacrylamide gel; and pre-stained standard lipoproteins (e.g., Lp(a); Large LDL; LDL-III; and LDL-IV) are applied to sample application slots on either side of the plasma application slot. The gel can be run at 125 V 12-18 hours, i.e., 125 volts can be applied to the gel for 12-18 hours. Alternatively, the following voltage gradient can be applied: 20V for 15 minutes, 40V for 15 minutes, 60V for 15 minutes, 80V for 15 minutes, and 125V for 15 minutes, for a total of 1 hour 15 minutes; and the voltage gradient re-applied continuously over the course of 12 hours. After application of the voltage for 12-18 hours, a portion of the gel that is in a position beyond (toward the cathode side of the gel) the position of the LDL-IV band is excised, creating a trough (FIG. 4); the trough is filled with buffer; and voltage (250V) is applied to the gel for approximately 30-60 minutes to allow components of the sample to enter the buffer-filled trough, forming an elution sample. The elution sample is then analyzed for the presence of the very high density, ultra small apolipoprotein B containing particles. Any convenient method, e.g., ion mobility analysis, can be used to test the "very high density, ultra small lipid depleted apolipoprotein B containing particle" present in the elution sample. Ion mobility analysis is described in, e.g., U.S. Patent Publication No. 2010/0213061. The presence in the particle of apoB-100 and cytokeratin 8 can be detected using antibodies specific for these components.

Detection Methods

The present disclosure provides various detection methods involving detection of a very high density, ultra small, lipid depleted apolipoprotein B containing particles. The present disclosure provides methods for detecting a very high density, ultra small, lipid depleted apolipoprotein B containing particle, as described herein, in a biological sample obtained from an individual. The methods generally involve contacting the biological sample with an antibody specific for apoB 100 and/or an antibody specific for cytokeratin-8; and detecting binding of the antibody to molecules in the sample. A subject isolated very high density, ultra small, lipid depleted apolipoprotein B containing particle can be used as a positive control in a subject detection method.

The presence in the biological sample of an amount of the very high density, ultra small, lipid depleted apolipoprotein B containing particle and/or cytokeratin 8 that is higher than a normal control amount can indicate that the individual from whom the biological sample was obtained has, or is at higher risk than the general population of developing, a disorder such as cardiovascular disease, atherosclerosis, myocardial infarction, or atherosclerotic plaque rupture, or is at risk of atherosclerotic plaque rupture. In some cases, the level of the very high density, ultra small, lipid depleted apolipoprotein B containing particle and/or cytokeratin 8 can provide an indication of the individual's prognosis following placement in the individual of a stent. In some cases, the level of the very high density, ultra small, lipid depleted apolipoprotein B containing particle and/or cytokeratin 8 can provide an indication of the individual's prognosis following coronary artery bypass graft surgery (CABG).

The present disclosure provides diagnostic assays for determining whether an individual has cardiovascular disease (CVD); assays for assessing an individual's response to therapy for a CVD or other drug treatment; and prognostic assays for determining the risk that an individual will develop CVD. A subject isolated very high density, ultra small, lipid depleted apolipoprotein B containing particle can be used as a positive control in a subject detection method. A subject isolated very high density, ultra small, lipid depleted apolipoprotein B containing particle can be used to generate a standard curve, for use in a subject detection method, e.g., where the detection is qualitative.

Detecting an Ultra-Small Apo B Containing Particles

A very high density, ultra small, lipid depleted apolipoprotein B containing particle as described above can be detected in a biological sample (e.g., blood, or a blood fraction such as serum or plasma). A very high density, ultra small, lipid depleted apolipoprotein B containing particle as described above, can be detected using, e.g., antibody specific for apoB and antibody specific for cytokeratin 8. An antibody specific for a component (e.g., an antibody specific for apoB-100; an antibody specific for cytokeratin 8) can comprise a detectable label. Suitable detectable labels include any composition detectable by ion Mobility, spectroscopic, photochemical, biochemical, immunochemical, electrical, optical, or chemical means. Suitable detectable labels include, but are not limited to, magnetic beads (e.g. Dynabeads™), fluorescent dyes (e.g., fluorescein isothiocyanate, texas red, rhodamine, a green fluorescent protein, a red fluorescent protein, a yellow fluorescent protein, and the like), a radiolabel (e.g., $^3$H, $^{125}$I, $^{35}$S, $^{14}$C, or $^{32}$P), an enzyme (e.g., horse radish peroxidase, alkaline phosphatase, luciferase, and others commonly used in an enzyme-linked immunosorbent assay (ELISA)), and colorimetric labels such as colloidal gold or colored glass or plastic (e.g. polystyrene, polypropylene, latex, etc.) beads.

An antibody specific for a component (e.g., an antibody specific for apoB-100; an antibody specific for cytokeratin 8) can be immobilized on a on a solid support. Suitable supports are well known in the art and comprise, inter alia, polystyrene beads, latex beads, magnetic beads, colloid metal particles, glass and/or silicon chips and surfaces, nitrocellulose strips, nylon membranes, sheets, duracytes, wells of reaction trays (e.g., multi-well plates), plastic tubes, etc.

In some cases, the average particle diameter size and the mass of the particle are determined following detection of the particle. The average particle diameter and mass of the particle can be determined using ion mobility analysis. See, e.g., U.S. Patent Publication No. 2010/0213061. Non-denaturing polyacrylamide gradient gel electrophoresis (see, U.S. Pat. No. 5,925,229). Agarose gel electrophoresis. Nuclear Magnetic Resonance (NMR), see U.S. Patent No. 20110004453. Density gradient ultracentrifugation. Electron microscope. Any method cable to count and measuring particles size not listed here.

The substantial lack of triglycerides and cholesterol can be determined using standard assays for these compounds. For example, methods involving use of enzymatic hydrolysis of triglycerides to glycerol and free fatty acids, followed by either colorimetric or fluorometric measurement of the glycerol released, can be used. For standard assays for triglycerides see, e.g., Bucolo and David (1973) *Clin. Chem.* 19:476; Fossati and Prencipe (1982) *Clin. Chem.* 28:2077; McGowan et al. (1983) *Clin. Chem.* 29:538; and Mendez et al. (1986) *Anal. Biochem.* 156:386. Various colorimetric and fluorometric assays for cholesterol are known in the art; and any such assay method can be used to determine substantial lack of cholesterol in an apoB/apoA-I particle as described herein. See, e.g., Kishi et al. (2002) *Clin. Chem.* 48:737, for an example of an assay for cholesterol.

The detection can be quantitative or qualitative. In some embodiments, e.g., where quantitative detection is desired, a standard curve using known amounts (e.g., 1 ng, 10 ng, 50 ng, 100 ng, 1 μg, 10 g, 50 μg, 100 μg, etc.) of a subject very high density ultra-small apo B containing particles is used.

Assessing Risk of CVD

The present disclosure method for assessing risk of CVD in an individual, the method comprising: detecting (e.g., measuring, determining, or assessing) a level of a very high density, ultra small, lipid-depleted apo B containing particle as described above in a biological sample from the individual; and assessing the risk based on the detected level of the particle. A level of the very high density, ultra small, lipid depleted apo B containing particle that is higher than a normal control level indicates that the individual has an increased risk of CVD. For example, a level of the "very high density, ultra small, lipid depleted apo B containing particle" that is at least 15% higher, at least 25% higher, at least 50% higher, at least 75% higher, at least 2-fold higher, at least 5-fold higher, or greater than 5-fold higher, than a normal control level indicates that the individual has an increased risk of CVD. CVD includes atherosclerosis, coronary artery disease (which may result in myocardial infarction), angina, stroke, hypertension, and heart failure. In some instances, the individual (e.g., a human) exhibits at least one clinical symptom or sign of cardiovascular disease.

A subject method of assessing risk of CVD can involve use of a subject kit (as described below), where the kit can include a positive control (e.g., a purified very high density ultra-small apo B containing particle, as described above) and/or components for generating a standard curve (e.g., a subject isolated very high density ultra-small apo B containing particle in defined amounts, e.g., 1 ng, 10 ng, 50 ng, 100 ng, 1 μg, 10 μg, 50 μg, 100 μg, etc.). For example, the level of the very high density, ultra small, lipid depleted apo B containing particle can be determined by comparison to a standard curve generated using a subject isolated very high density ultra-small apo B containing particle in defined amounts.

Based on a subject detection method, a certain therapeutic regimen may be recommended by a physician or other qualified medical personnel. For example, where the outcome of subject detection method indicates that the individual has an increased risk, compared to a healthy individual who has no signs of CVD, of developing CVD, a recommendation as to pharmaceutical intervention, diet alteration, exercise regimen, and the like, may be made.

In some cases, a subject method of assessing risk of CVD can further include communicating to the individual from whom the biological sample was obtained (in which biological sample the level of the very high density ultra-small apo B containing particle was detected) the results of the assessment and/or suggested treatment regimens. Thus, in some embodiments, a subject method comprises detecting a level of a very high density, ultra small, lipid depleted apo B containing particle as described above in a biological sample from the individual; assessing the risk that the individual has or will develop CVD based on the detected level; and communicating a recommended treatment regimen to the individual. The recommended treatment regimen can be based on a therapy decision tree that sets forth various treatment options, depending on the results of the subject method, and optionally other patient information (e.g., results of other tests, such as other tests for CVD; patient medical history; any prior or ongoing treatment the patient is undergoing; etc.).

In some embodiments, a subject method of assessing risk of CVD can further include treating the individual for CVD. For example, an individual determined to be a higher risk of CVD than the general population can be treated with a blood pressure-lowering drug (e.g., a diuretic; a beta blocker), an anti-coagulant drug, or a cholesterol-lowering drug. For example, an individual determined to be a higher risk of CVD than the general population can be treated with: 1) a diuretic, e.g., a thiazide diuretic; 2) a beta blocker (e.g., Sectral (acebutolol); Zebeta (bisoprolol); Bevibloc (esmolol); Inderal (propranolol); Tenormin (atenolol); Normodyne (labetalol); Coreg (carvedilol); Lopressor (metoprolol)); 3) an anti-coagulant such as Coumadin (warfarin), Heparin, Lovenox, or Fragmin; or 4) a cholesterol-lowering drug such as a HMG-CoA reductase inhibitor (a statin) (e.g., atorvastatin (Lipitor), fluvastatin (Lescol), lovastatin (Mevacor), pitavastatin (Pitava), pravastatin (Pravachol), rosuvastatin (Crestor), simvastatin (Zocor)), or a fibrate (e.g., gemfibrozil (Lopid), fenofibrate (Tricor), or fenofibric acid (Trilipix).

A subject method of assessing risk of CVD can further include generating a report that provides an indication of the risk that the individual will develop CVD. A "report," as described herein, is an electronic or tangible document that includes report elements that provide information of interest relating to a likelihood assessment and its results. A subject report includes at least a likelihood assessment, e.g., an indication as to the risk that an individual will develop CVD. A subject report can be completely or partially electronically generated, e.g., presented on an electronic display (e.g., computer monitor). A report can further include one or more of: 1) information regarding the testing facility; 2) service provider information; 3) patient data; 4) sample data; 5) an interpretive report, which can include various information including: a) indication; b) test data, where test data can include the level of very high density, ultra small, lipid depleted apo B containing particles and a normal control level of very high density, ultra small, lipid depleted apo B containing particles and 6) other features.

Thus, in some embodiments, the methods of the present disclosure further include generating a report that includes information regarding the patient's likely clinical outcome, e.g. risk of CVD. For example, the methods disclosed herein can further include a step of generating or outputting a report providing the results of a subject risk assessment, which report can be provided in the form of an electronic medium (e.g., an electronic display on a computer monitor), or in the form of a tangible medium (e.g., a report printed on paper or other tangible medium).

Assessing Efficacy of Treatment

The present disclosure provides a method of assessing the efficacy of a treatment for a cardiovascular disease in an individual. In some cases, the method comprises: a) analyzing the level of a very high density, ultra small, lipid depleted apo B containing particles (as described above) in a biological sample obtained from the individual following the treatment; and b) comparing the post-treatment level to a pre-treatment level. A post-treatment level that is lower than the pre-treatment level indicates that the treatment was efficacious.

In some cases, a method of assessing efficacy of therapy involves analyzing the level of very high density, ultra small, lipid depleted apo B containing particles (as described above) in a biological sample obtained from an individual at a first time point during treatment for a CVD; analyzing the level of very high density, ultra small, lipid depleted apo B containing particles (as described above) in a biological sample obtained from an individual at a second time point (where the second time point is later than the first time point) during treatment for a CVD; and comparing the level from the first and second time points. A level at the second time point that is lower than the level at the first time point indicates that the treatment was efficacious. The second time point can be from one day to one week, from one week to one month, from one month to three months, from three months to six months, or more than six months, later than the first time point.

Determining Risk of Mortality

The present disclosure provides a method of determining the risk of mortality due to a CVD in an individual. The method comprises detecting a level of very high density, ultra small, lipid depleted apo B containing particles (as described above) in a biological sample from the individual. A level of the particle that is higher than a normal control level indicates that the individual has an increased risk of mortality due to a CVD.

Kits

The present disclosure provides a kit (e.g., a test kit) for use in carrying out a subject detection method. A subject kit includes an antibody specific for apoB-100 and an antibody specific for cytokeratin 8. The antibodies can be in separate containers. The antibodies can be immobilized on a solid support. The antibodies can be detectably labeled.

The antibodies can be immobilized on a solid support. Suitable supports are well known in the art and comprise, inter alia, commercially available column materials, polystyrene beads, latex beads, magnetic beads, colloid metal particles, glass and/or silicon chips and surfaces, nitrocellulose strips, nylon membranes, sheets, duracytes, wells of reaction trays (e.g., multi-well plates), plastic tubes, etc. A solid support can comprise any of a variety of substances, including, e.g., glass, polystyrene, polyvinyl chloride, polypropylene, polyethylene, polycarbonate, dextran, nylon, amylose, natural and modified celluloses, polyacrylamides, agaroses, and magnetite. Suitable methods for immobilizing a subject antibody onto a solid support are well known and include, but are not limited to ionic, hydrophobic, covalent interactions and the like. Solid supports can be soluble or insoluble, e.g., in aqueous solution. In some embodiments, a suitable solid support is generally insoluble in an aqueous solution.

In some embodiments, a subject kit includes an antibody specific for apoB-100 and an antibody specific for cytokeratin 8, where each antibody is immobilized on a solid support, such as a test strip.

An antibody included in a subject kit will in some embodiments comprise a detectable label. Suitable detectable labels include any composition detectable by spectroscopic, photochemical, biochemical, immunochemical, electrical, optical or chemical means. Suitable include, but are not limited to, magnetic beads (e.g. Dynabeads™), fluorescent dyes (e.g., fluorescein isothiocyanate, texas red, rhodamine, a green fluorescent protein, a red fluorescent protein, a yellow fluorescent protein, and the like), radiolabels (e.g., $^3$H, $^{125}$I, $^{35}$S, $^{14}$C, or $^{32}$P), enzymes (e.g., horse radish peroxidase, alkaline phosphatase, luciferase, and others commonly used in an ELISA), and colorimetric labels such as colloidal gold or colored glass or plastic (e.g. polystyrene, polypropylene, latex, etc.) beads.

A subject kit can further include reagents for detecting triglycerides; reagents for detecting cholesterol; etc. Other optional components of the kit include: a buffer; a protease inhibitor; a detectable label; etc. The various components of the kit may be present in separate containers or certain compatible components may be pre-combined into a single container, as desired.

In addition to above-mentioned components, a subject kit can include positive controls (e.g., a purified very high density ultra-small apo B containing particle); and/or components for generating a standard curve (e.g., a subject isolated very high density ultra-small apo B containing particles in defined amounts, e.g., 1 ng, 10 ng, 50 ng, 100 ng, 1 µg, 10 µg, 50 µg, 100 µg, etc.).

In addition to above-mentioned components, a subject kit can include instructions for using the components of the kit to practice a subject method. The instructions for practicing a subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. compact disc-read only memory (CD-ROM), digital versatile disk (DVD), diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Isolation and Characterization of Very High Density, Ultra Small, Lipid Depleted Apo B Containing Particles Materials and Methods Materials Monoclonal apo B antibody M-035 (cat #H45640M, concentration 4.61 mg/mL, lot #7821) and M-036 (Cat #H45161M, concentration 2.1 mg/mL, lot #4A03107) from Meridian Life Science, Saco, Me. 04072, USA. Dynabeads M-280 Tosylactivated magnetic beads cat #142-04 from Invitrogen, Carlsbad, Calif. 92008, USA.

Polyacrylamide gradient gels (2-14%), with 18 sample loading lanes, were produced locally at the Children's Hospital Oakland Research Institute (CHORI), Oakland, Calif. 94609, USA. Electrophoresis chamber with power supply and cooling device was from Pharmacia Company, Stockholm, Sweden. Concentrated electrophoresis buffer was made in-house according to a standard operating procedure; 217.93 grams (gm) trizma base (Tris-hydroxymethyl aminomethane), 98.88 gm boric acid, 20.20 gm di-sodium EDTA in 4000 mL double deionized water. The working solution was made by diluting the concentrated buffer 1 in 5 (600 ml concentrated buffer+2400 double deionized water).

Sudan black stain was from Beckman-Coulter, Fullerton, Calif., USA. Lipoprotein particle size calibrator or quality control (LPCAL: AE/AG) was made in-house, and provided the following range of particle sizes: 315, 275.8, 248.7, and 225.2 Å. Sample application comb was from Pharmacia, Stockholm, Sweden. Centricon-10 (cat #4206) 2 ml-concentrator was from Amicon, Billerica, Me., USA.

Other reagents and product were obtained from the following sources: 1) Coomassie blue (cat #6104-58-1) (Sigma, St. Louis, Mo., USA); 2) Airborne ion mobility analyzer (TSI incorporation, Minnesota, USA); 3) Cholesterol reagent (cat #E33940), (Polestar Laboratory, Escondido, Calif., USA); 4) Free Glycerol Reagent A (Sigma,cat. No. F6428, 40 ml); 5) Triglyceride Reagent B (Sigma, cat. No. T2449, 10 ml); and 6) Bradford protein assay (Bio-Rad, cat. No. #500-0202, Hercules, Calif. 94547).

A monoclonal specific antibody against apoB-100, (catalogue No. K90086P), and horseradish peroxidase (HRP) conjugated secondary (anti-IgG) antibody, were obtained from Biodesign International, a division of Meridian Life Science Inc, Saco, Me. 04072, USA.

Additional reagents and products were obtained from the following sources: 1) Super-signal developing reagent kit, (catalogue No. 34096), from Pierce, Rockford, Ill. 61105, USA; 2) X-ray film, (catalogue No. EK8FL), Belgium; 3) X-ray film developing equipment from Kodak, Rochester, N.Y.; 4) Bovine albumin (>99% purity), (catalogue No. A-6003) from Sigma, St. Louis, Mo., USA; 5) Glycine, (catalogue No. G7126) from Sigma; 6) Methanol, (catalogue No. M1775) from Sigma-Aldrich, St Louis, Mo., USA; 7) Trizma-base (Hydroxymethyl aminomethane), (catalogue No. T1503) from Sigma-Aldrich; 8) sodium dodecyl sulfate (SDS) gel 3-8% and 4-20% (catalogue No. EC60385) from Invitrogen, Carlsbad, Calif. 92008, USA; 9) SDS reducing agent (catalogue No. NP0009) from Invitrogen; 10) SDS tracking dye (catalogue No. NP0007) from Invitrogen; 11) SDS running buffer, (catalogue No. NP0001) from Invitrogen; 12) Antioxidant, (catalogue No. NP0005) from Invitrogen; 13) Nitrocellulose transfer membrane, (catalogue No. 13849) from Bio-Rad, Hercules, Calif., 94547, USA; 14) Tween-20 detergent, (catalogue No. P1379) from Sigma-Aldrich; 15) Phosphate buffered saline (PBS) made according to the laboratory standard operating protocol, CHORI, Oakland, Calif., USA; 17) Pre-stained proteins molecular weight standard (10-250 KDA), (catalogue No. 161-0375) from Bio-Rad, Hercules, Calif., USA and 27-180 KDA from Sigma, catalogue #MW-SDS-Blue; 18) Unstained proteins molecular weight (40-500 KDA) standard, (catalogue No. LC5688) from Invitrogen; 19) ApoB-100 and apoB-48 standard prepared in-house; 20) Brilliant Blue G (Coomassie blue) stain, (catalogue No. B0770) from Sigma; 21) SDS gels de-staining solution made according to the laboratory standard operating protocol; 22) Polyclonal specific antibody against cytokeratin 8, (catalogue No. RB-9095-PO) from Labvission, Fremont, Calif., USA; and 23) Cytokeratin 8 positive control, (catalogue No. RB-9095-PCL) from Labvission, Fremont, Calif., USA.

Methods

Separation of Very High Density, Ultra Small, Lipid Depleted Apo B Containing Particles by Immunoaffinity Apo B was conjugated to the Dynabeads® M-280 Tosy-lactivated using manufacturer recommended procedure with slight modification such as replacing the bovine serum albumin (BSA) in buffer D with non-fat dry milk powder, replacing BSA in buffer E with Tween 20 and antibody conjugation temperature from 37° C. for 12-18 hours to 22-25° C. for 24 hours. Samples were diluted 1:200 in buffer D and incubated with beads conjugated with apo B-specific antibody at 25° C. with continuous rocking for 30 minutes. At the end of the incubation period, a magnetic field was applied to the tubes, then the supernatant was removed, followed by 3 washes with phosphate buffer saline (PBS). Glycine buffer (pH 2.8) was used to elute the apo B particles. Then the pH was immediately adjusted to around 7.0 with 2 µL of the 2.5 mmol NaOH. The eluted particles were dialyzed over night against 25 mmol ammonium acetate before analysis by ion mobility.

Isolation of Very High Density, Ultra Small, Lipid Depleted ApoB Containing Particles by Ultracentrifugation Plasma density adjustment: The density of the plasma was adjusted to 1.21 g/mL (by adding 1.91 gram NaBr to 6.503 mL plasma) and to 1.25 g/L (by adding 2.294 gram NaBr to 6.4 mL plasma). After completely dissolving NaBr into the plasma, 6 mL was taken and added to the ultracentrifuge tubes, then 6 µL 10 mmol trolox was added to each tube to prevent lipoproteins oxidation. Mock solution density adjustment: The density of the mock solution was adjusted to 1.21 g/mL (by adding 1.91 gram NaBr to 6.503 mL plasma) and to 1.25 g/L (by adding 2.294 gram NaBr to 6.4 mL plasma). After complete dissolution of NaBr into the mock solution, 6 mL was taken and added to the ultracentrifuge tubes, then 6 µL 10 mmol trolox was added to each tubs for reason of treating these tubes equally to the plasma tubes. These tubes served as balance in the ultracentrifuge and also for density verification for the plasma tubes. Ultracentrifugation was carried out at 40,000 rpm (average 115,046 g force), at 15° C. for 24 hours. At the end of the ultracentrifugation, the tubes were carefully removed and the top 1.5 mL was harvested from the all tubes (plasma and mock solution). Densities of the top and bottom fractions of the mock solution tubes were measured by the densitometer. The top and bottom fractions were dialyzed against 25 mmol ammonium acetate for approximately 24 hours at 4° C. Following the dialysis of the plasma fractions, ion mobility was used to measure particle size. In addition, the concentration of apoB was measured by ELISA assay using monoclonal specific antibody.

Isolation of Very High Density, Ultra Small, Lipid-depleted Apo B Containing Particles by Gradient Gel Electrophoresis (GGE)

A pre-staining lipoprotein standard with known peak particles size (Å) was prepared as follows prior to carrying out the procedure: Sudan black 'Lipostain' (Beckman Coulter) was added to the lipoprotein standard to make a 4% (v/v) solution (4 µl Lipostain+96 µl lipoprotein standard). This was then incubated overnight (~12 h) and was used within one week.

A pre-staining lipoprotein standard with known peak particles size (Å) was prepared as follows prior to carrying out the procedure: Sudan black 'Lipostain' (Beckman Coulter) was added to the lipoprotein standard to make a 4% (v/v) solution (4 µl Lipostain+96 µl lipoprotein standard). This was then incubated overnight (~12 h) and was used within one week.

The electrophoresis buffer was cooled to a temperature between 8-16° C. The gel (2-14%) was pre-electrophoresed at 125 volts for at least 30 minutes to remove any particulates and to condition the gel with electrophoresis buffer. A pre-stained lipoprotein standard with known particle size was applied (10 µL) to lanes 1, 2, 17 and 18. Plasma samples (10 µL) were applied to lanes 3 through 16. Electrophoresis was carried for 15 minute intervals at 20, 40, 60, and 80V, and at 125V overnight (12 hours).

A scalpel or a razor blade was used to remove the top section of the gel (~1-3 mm) to remove any proteins or albumin that might have been trapped with the VLDL fraction in this part of the gel. The gel was then re-loaded using fresh electrophoresis buffer and electrophoresis was carried out at 250V for an additional 2 hours.

At the end of the 2 hours, a scalpel or razor blade and a ruler was used to excise the gel and create a window below the LDL-IV band (225 Å) with an approximate width of 0.5 cm. A length of about 0.5 cm was left on the side of the window to hold the upper and lower parts of the gel together (see FIG. 4). The window was filled with 1× Trizma Borate EDTA (TBE) buffer and was covered with a dialysis membrane to prevent buffer leakage.

The gel cassette was then re-assembled and re-inserted into the upper electrophoresis chamber, and electrophoresis was continued at 250 volts for 45 minutes to collect fraction 1. Then the gel cassette was opened to collect the first fraction by aspiration using plastic transfer pipette. This aspiration was repeated a few times to ensure that all particles belonging to that fraction were collected.

The cassette was re-assembled and re-loaded again into the GGE chamber and electrophoresis was continued at 250 volts for intervals of 1 hour until all of the LDL fractions of interest had been separated and collected. The volume of each fraction was approximately 500 µl from each gel and the total volume from 4 gels was 2 mL.

The collected fractions were then concentrated by centrifugation at 7,000 rpm for 60 minutes at a temperature of 4° C. using the 2 ml concentrator Centricon-10 to reduce the volume to approximately 500 µl (4× concentration). To verify the uniformity of the final collected fractions, they were separated a second time by electrophoresis on a new 2-14% gradient gel, and by an ion mobility analyzer, for the measurements of their particles size diameter.

Ion Mobility (IM)

An ion mobility analyzer was used as an additional tool to test the eluted lipoprotein particles as described by Caulfield et al 2008.

Molecular Weight Determination of Proteins by SDS-PAGE

SDS polyacrylamide gel electrophoresis (SDS-PAGE) was used to identify proteins associated with the LDL-IV fraction according to their molecular weight. First the protein concentration was measured with Bradford protein assay (0.158 µg/mL; assay sensitivity 0.125-2.0 mg/ml) then the proteins of interest were separated and stained on SDS-PAGE as described by the kit manufacturer (Invitrogen, CA, USA).

Protein Transfer Procedure

Following the separation of proteins by SDS-PAGE as described above, the proteins were transferred to a nitrocellulose membrane for immunoblotting as described by the kit manufacturer (Invitrogen, CA, USA.

Immunoblotting

The manufacturer procedure was modified/optimized and carried out as follows.

Bovine Serum Albumin (BSA) (3%) was made with PBS buffer, then 25 µl of Tween-20 was added to 50 ml of 3% bovine albumin (0.05%) and the membrane was incubated with gentle shaking at room temperature or overnight at 4° C.

The membrane was incubated, with shaking, with an apoB-specific primary antibody diluted 1: 10,000 with 3% BSA containing Tween-20 at a concentration of 0.05% at 300 revolutions for 2 hours at RT or overnight in the cold room. The 0.3% BSA containing 0.05% Tween-20 was used as a washing buffer to wash the membrane on three occasions, at 10 minutes for each wash, to remove all non-specific binding of antibodies. The membrane was incubated with secondary apoB HRP conjugated antibody (diluted 1:5000) for 1 hour at room temperature (RT). The membrane was washed 5 times, with shaking, using the washing buffer described above, at 300 revolutions for 10 minutes for each wash to remove any non-specific binding.

The membrane was developed using the super signal reagent, prepared by adding 1 ml Reagent One to 1 ml Reagent Two in 8 ml distilled water. The membrane was then soaked in the super signal reagent for 2-5 minutes, after which, the developed membrane was placed between two layers of clear thin plastic. The membrane was exposed to x-ray film for 10, 20, 30, 60, and 90 seconds. The exposed films were then developed and examined.

Determination of Molecular Mass of the 52 kDa band by mass spectrometry (MS)

Mass spectrometry was performed at Stanford University, Palo Alto, Calif., USA, according to their laboratory standard operating procedure (Shevchenko et al, 1996, 2007). The very high density, ultra small, lipid depleted apo B containing particles were separated and stained after SDS-PAGE as described above and in-gel trypsin digestion and protein analysis of the ≈52 kDa band by MS was performed.

Results

The immunoaffinity procedure was employed using monoclonal apo B antibody to isolate very high density, ultra small, lipid depleted apo B containing particles directly from plasma. The isolated particles were analyzed by ion Mobility as shown in FIG. 1.

Figure 3:
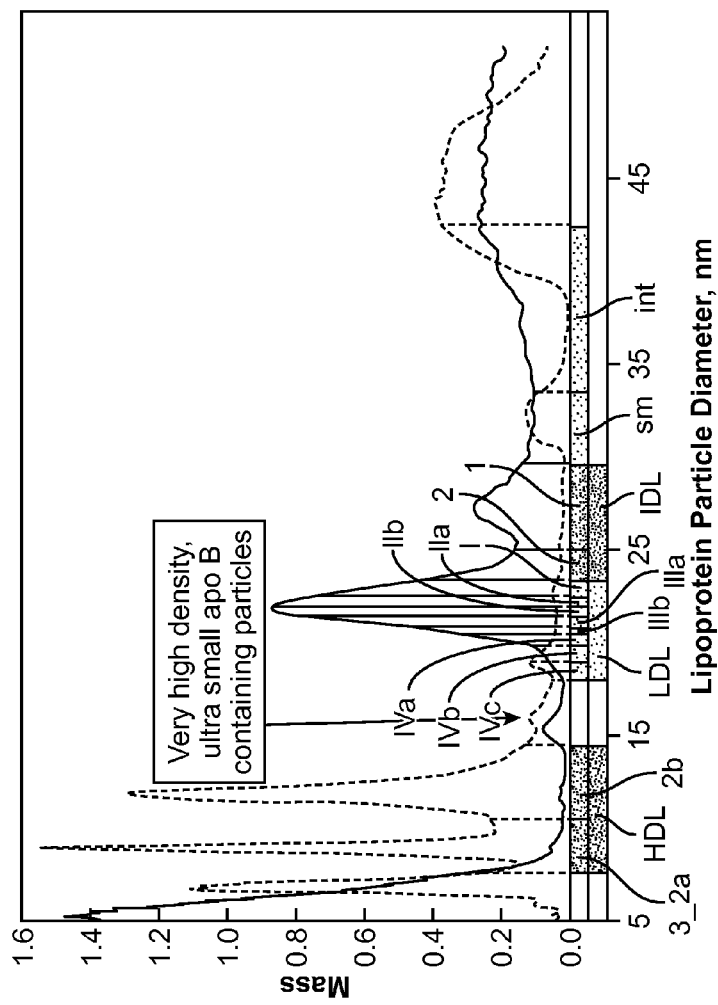
FIG. 3 depicts ion mobility analysis of the apoB-containing lipoproteins isolated from the ultracentrifugal fractions described in FIG. 2 using a specific anti-apoB antibody conjugated to magnetic beads.

Following the ultracentrifugal separation, dialysis and appropriate dilution of the top and bottom fractions of the very high density solution containing the sample of interest, the following results were obtained by ion Mobility as shown in FIG. 2. Also the immunoaffinity procedure was used to isolated apo B containing particles from the top 1.5 mL of the 1.25 g/mL density (black line) and from the bottom 4.5 mL of the 1.25 g/mL density (blue line) ultracentrifuged sample and then the eluted particles were analyzed by ion Mobility as shown in FIG. 3. The ELISA results for apoB in the top and bottom density fractions are shown in Table 1.

TABLE 1

| Density 1.21 g/mL | Dilution factor | Concentration factor | apo B concentration | final apo B result |
|---|---|---|---|---|
| Top fraction | 1.08 | 4 | 219.6 | 59.3 |
| Bottom fraction | 1.08 | 1.3 | 7.2 | 6.0 |
| Top + Bottom | | | | 65.3 |
| Original Plasma | N/A | N/A | 80 | 80 |
| Recovery | | | | 82% |

TABLE 2 apo B recovery calculation in comparison to the original plasma concentration; some losses may be attributed to adhesion to the ultracentrifuge tube.

FIG. 1. IM profile showing the total apo B containing particles following immunoaffinity isolation (directly from the plasma) using monoclonal apo B antibody.

FIG. 2. IM profile showing LDL and HDL (blue line) isolated from the 1.5 mL top fraction of 1.21 g/mL and the very high density ultra small particles (black line) isolated from the 4.5 mL bottom 1.21 g/mL.

FIG. 3. IM profile showing immunoaffinity isolated apo B containing particles from the top 1.5 mL of the 1.25 g/mL density (black line) and from the bottom 4.5 mL of the 1.25 g/mL density (blue line) ultracentrifuged sample.

Since the gel elution method released the smaller and denser particles first, the fraction numbers were inversely related to LDL fractions as defined by increasing density in the ultracentrifugation i.e. I to IV. The gel elution fractions start at 1, 2, 3, 4, and 5, moving from smaller and denser particles to the larger and more buoyant particles, in which fraction 1 corresponds to the very high density, ultra small, lipid depleted apo B containing particles) (F1), fraction 2 to LDL-IV (F2), fraction 3 to LDL-III (F3), while fractions 4 and 5 correspond to the larger LDL's (F4 and F5).

Ion Mobility Analysis

Figure 5:
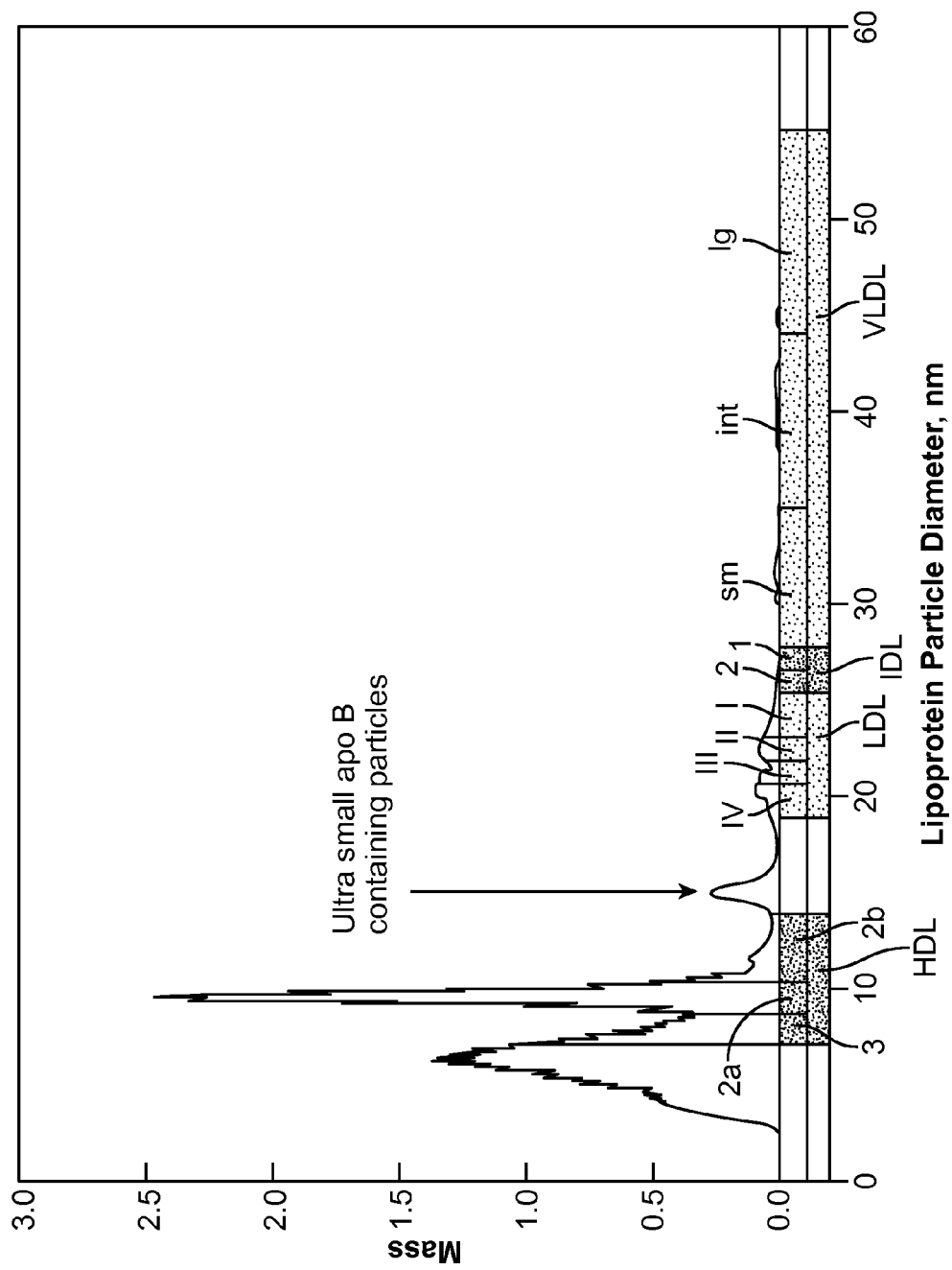
FIG. 5 depicts ion mobility analysis of particles isolated by electrophoresis in fraction 1 from the elution window shown in FIG. 4.
Figure 6:
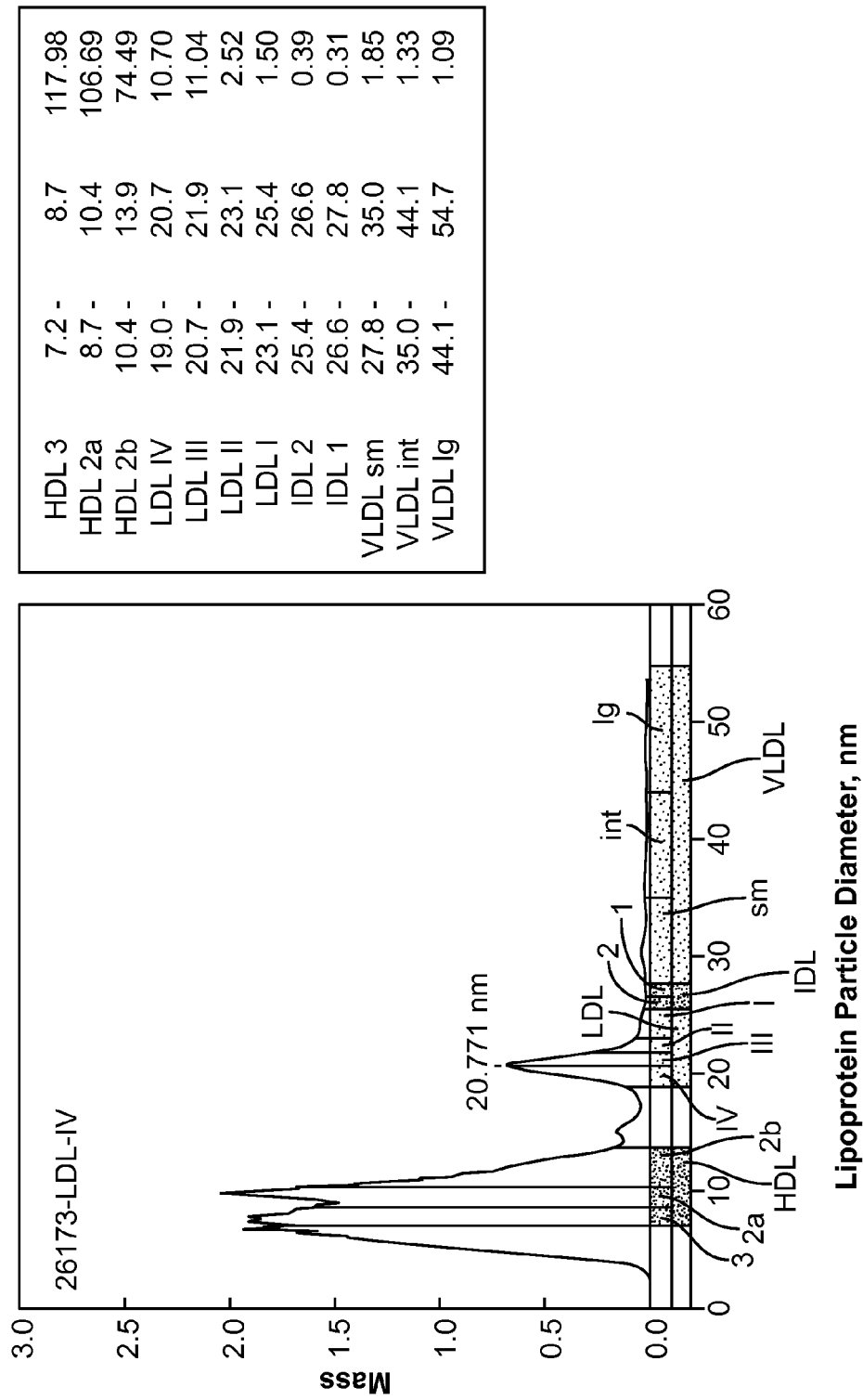
FIG. 6 depicts ion mobility analysis of particles isolated by electrophoresis in fraction 2 from the elution window shown in FIG. 4.
Figure 7:
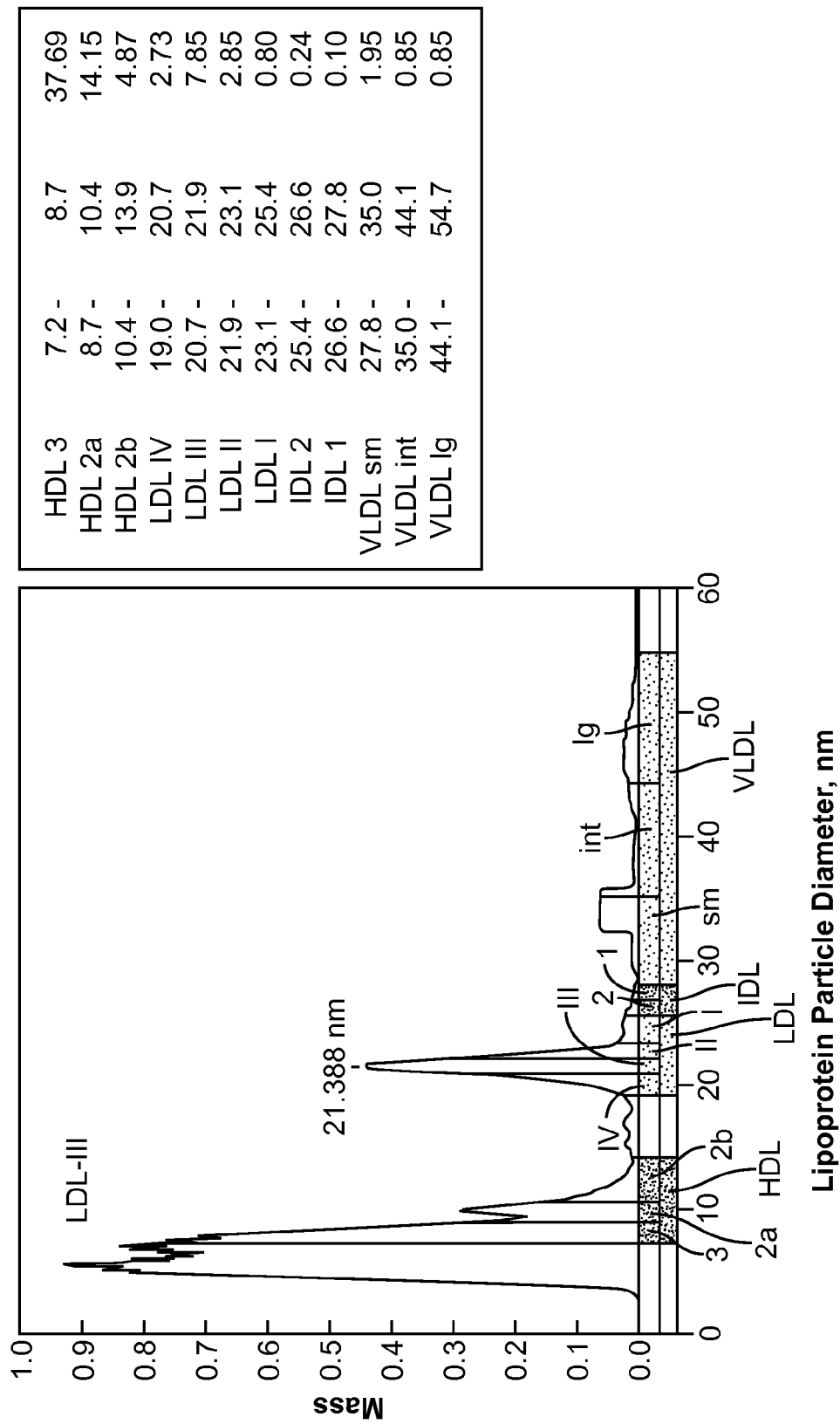
FIG. 7 ion mobility analysis of particles isolated by electrophoresis in fraction 3 from the elution window shown in FIG. 4.

The characteristics of the particles in the separated fractions, namely very high density, ultra small, lipid depleted apo B containing particles), LDL-IV and LDL-III, were confirmed by ion mobility analysis as shown in FIG. 5, FIG. 6, and FIG. 7.

Figure 4:
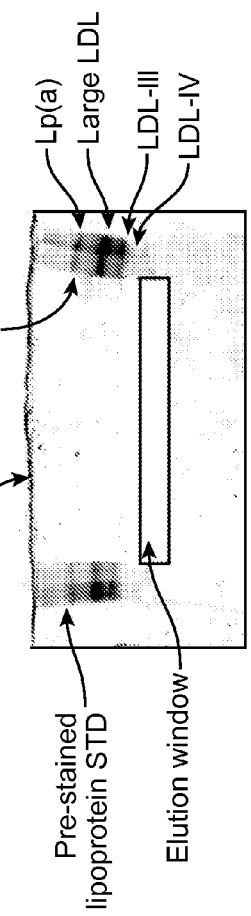
FIG. 4 displays a 2-14% gradient polyacrylamide gel, showing the elution window with pre-stained lipoprotein standards.

FIG. 5 depicts ion mobility analysis of particles isolated by electrophoresis in fraction 1 from the elution window shown in FIG. 4.

FIG. 6 depicts ion mobility analysis of particles isolated by electrophoresis in fraction 2 from the elution window shown in FIG. 4.

Figure 8:
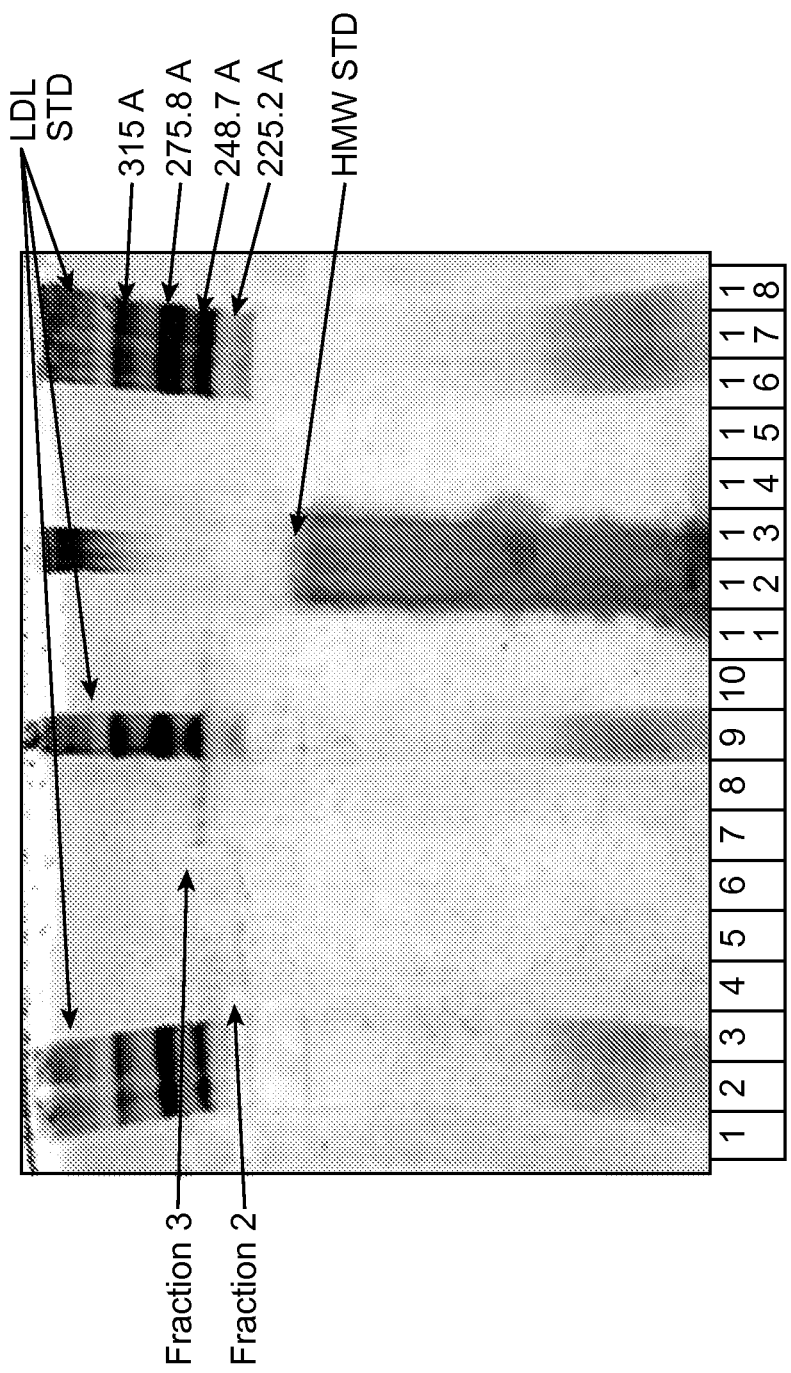
FIG. 8 depicts the results of 2-14% gradient gel electrophoresis (GGE), followed by lipid staining with Sudan Black, of fractions 2 and 3 described in FIGS. 6 and 7. Lanes 1, 2, 8, 17 & 18, lipoprotein standards; lanes 3-5, fraction 2; lanes 6 & 7, fraction 3; lanes 9-12, empty; lane 13, high molecular weight protein standards; lanes 14-16, empty.

FIG. 7 ion mobility analysis of particles isolated by electrophoresis in fraction 3 from the elution window shown in FIG. 4. Fractions on 2-14% gradient gels FIG. 8 depicts the results of 2-14% gradient gel electrophoresis (GGE), followed by lipid staining with Sudan Black, of fractions 2 and 3 described in FIGS. 6 and 7. Lanes 1,2, 8, 17 & 18, lipoprotein standards; lanes 3-5, fraction 2; lanes 6& 7, fraction 3; lanes 9-12, empty; lane 13, high molecular weight protein standards; lanes 14-16, empty.

Figure 9:
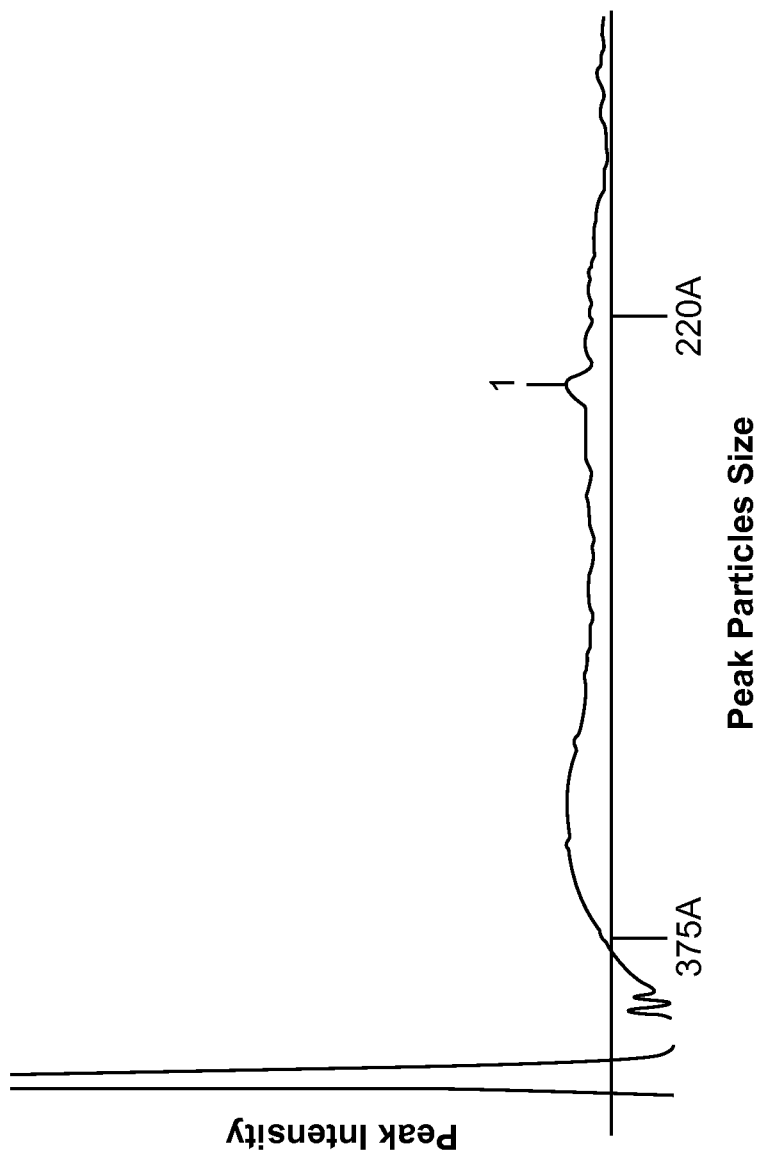
FIG. 9 depicts the densitometric scan of lane 3 in FIG. 8.

FIG. 9 depicts the densitometric scan of lane 3 in FIG. 8.

Figure 10:
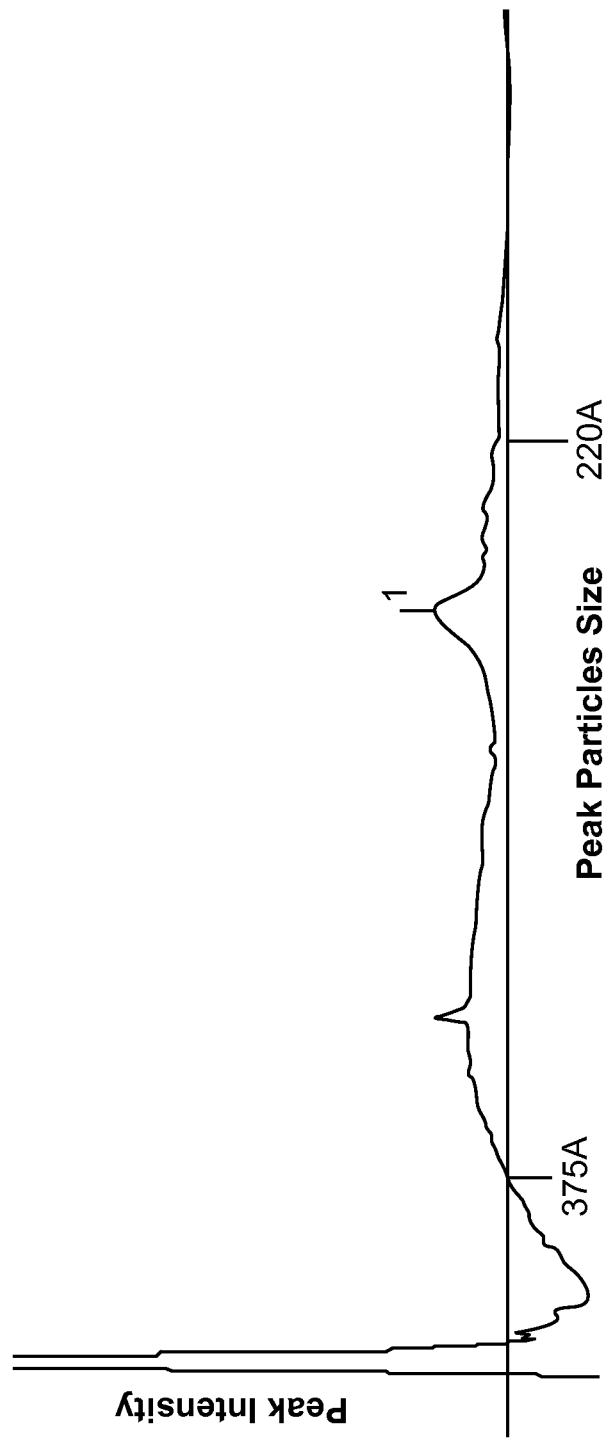
FIG. 10 depicts the densitometric scan of lane 4 in FIG. 8.

FIG. 10 depicts the densitometric scan of lane 4 in FIG. 8.

Figure 11:
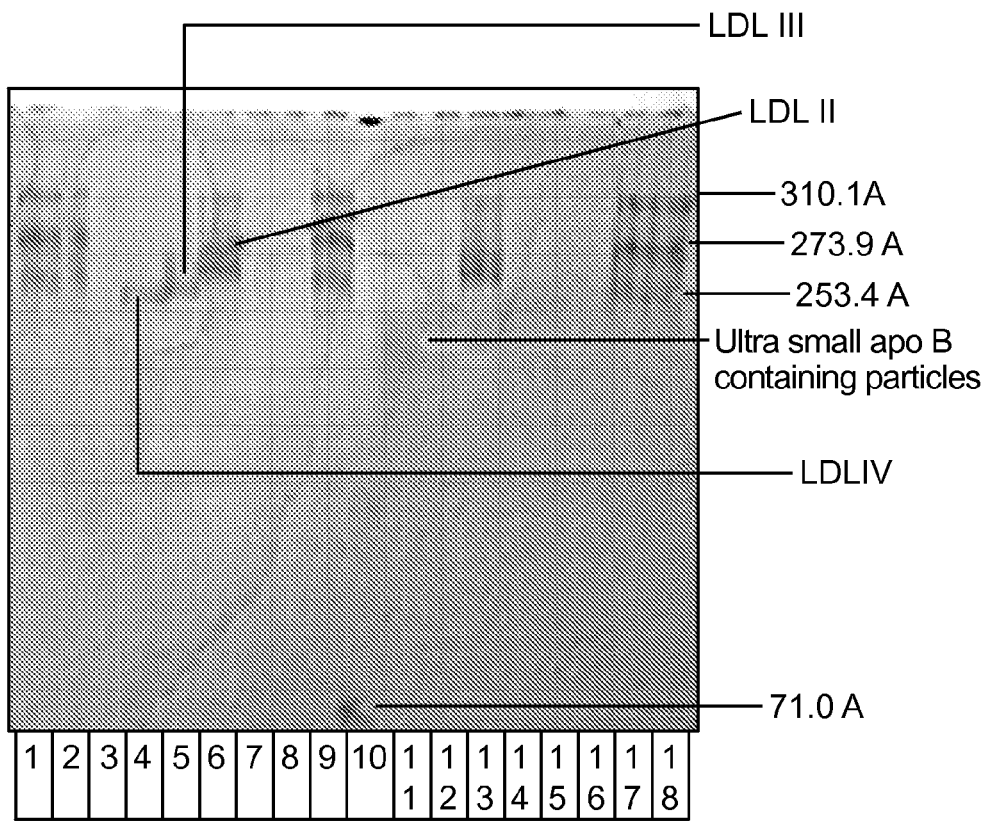
FIG. 11 depicts a 2-14% GGE stained with Coomassie blue of fractions 1, 2 and 3 from the elution window shown in FIG. 4. Lanes 1, 2, 9, 17 & 18, lipoprotein standards; lanes 4-6, fraction 2, 3 and 4; lanes 3, 7, 8, 15 and 16, empty; lane 10, bovine serum albumin; lane 13, LDL control; lanes 11, 12 and 14, ultra small apo B containing particles.

FIG. 11 depicts a 2-14% GGE stained with Coomassie blue of fractions 1, 2 and 3 from the elution window shown in FIG. 4. Lanes 1,2, 9, 17 & 18, lipoprotein standards; lanes 4-6, fraction 2, 3 and 4; lanes 3, 7, 8, 15 and 16, empty; lane 10, bovine serum albumin; lane 13, LDL control; lanes 11, 12 and 14, ultra small apo B containing particles.

Figure 12:
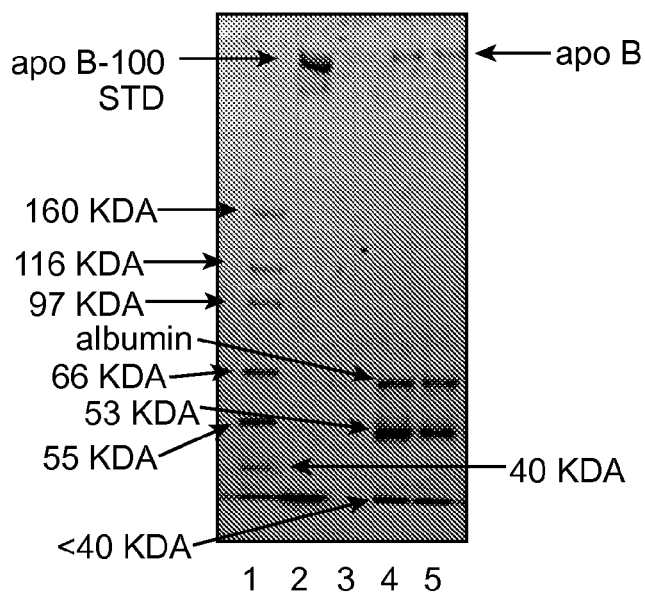
FIG. 12 depicts a sodium dodecyl sulfate (SDS) polyacrylamide of fraction 1 from the elution window shown in FIG. 4. Lane 1, molecular weight standard, lane 2, apo B-100 control, lane 3 empty; lane 4 and 5, ultra small apo B containing particles.

FIG. 12 depicts a sodium dodecyl sulfate (SDS) polyacrylamide of fraction 1 from the elution window shown in FIG. 4. Lane 1, molecular weight standard, lane 2, apo B-100 control, lane 3 empty; lane 4 and 5, ultra small apo B containing particles.

Western Immunoblotting for ApoB-100 Identification

Figure 13:
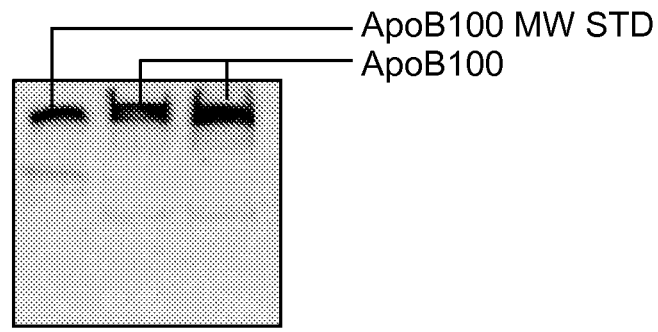
FIG. 13 depicts apoB-100 immunoblotting of fraction 1 samples derived from two individuals (lanes 2 and 3)
Figure 14:
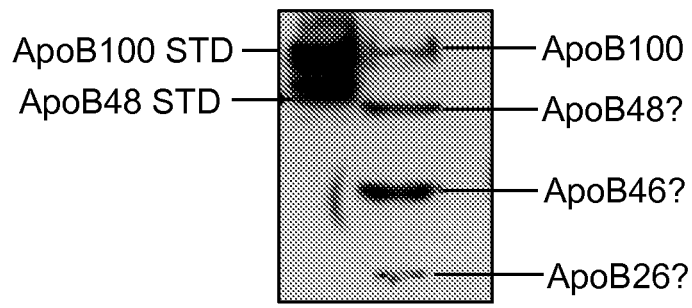
FIG. 14 depicts apoB-100 immunoblotting of fraction 1 samples derived from a third individual.

FIG. 13 depicts apoB-100 immunoblotting of fraction 1 samples derived from two individuals (lanes 2 and 3), FIG. 14 depicts apoB-100 immunoblotting of fraction 1 samples derived from a third individual.

Cytokeratin 8

Figure 15:
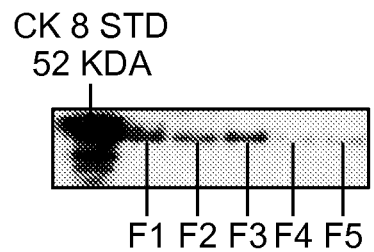
FIG. 15 depicts cytokeratin 8 (CK8) immunoblotting of fractions 1-5 (F1 to F5) isolated from a single individual using the elution window described in FIG. 4. First left lane, CK standard; lanes F1 to F5, fractions 1 to 5.

The specific antibody against cytokeratin "8" reacted, to a variable extent, with ≈53 KDA protein band blotted from the very high density, ultra small, lipid depleted apo B containing particles (F1), LDL-IV (F2), LDL-III (F3) and Lp(a), but not with LDL-II (F4) and LDL-I (F5) fractions eluted with GGE method and separated on SDS-PAGE (FIG. 15). Cytokeratin "8" was blotted from the 53 kDa bands of the very high density, ultra small, lipid depleted apo B containing particles eluted from 5 different plasma samples, and against the whole plasma. The first two subjects on the left side in FIG. 16 were recognized as LDL subclass pattern 'B' with predominantly small dense LDL, while the other three subjects were pattern 'A'. In the whole plasma sample, the cytokeratin "8" antibody reacted with the proteins corresponding to cytokeratin "8" in terms of its molecular weight and the molecular weight standard (STD), in addition to the presence of some other bands on the same, whole plasma lane. The appearance of the other additional bands may have been due to non-specific binding or to the presence of other cytokeratins with a homologous peptide sequence to cytokeratin "8".

FIG. 15 depicts cytokeratin 8 (CK8) immunoblotting of fractions 1-5 (F1 to F5) isolated from a single individual using the elution window described in FIG. 4. First left lane, CK standard; lanes F1 to F5, fractions 1 to 5.

Figure 16:
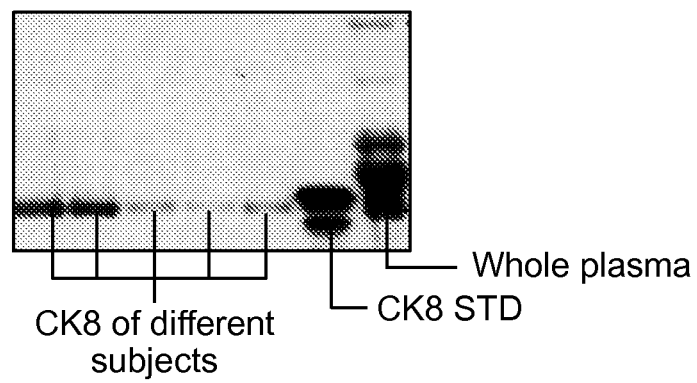
FIG. 16 depicts cytokeratin 8 immunoblotting of fraction 1 isolated from 5 individuals as described in FIG. 4.

FIG. 16 depicts cytokeratin 8 immunoblotting of fraction 1 isolated from 5 individuals as described in FIG. 4. Additionally, the CK "8" antibody was tested against whole plasma. The first two subjects on the left side are recognized as having LDL subclass pattern B, with respect to the distribution of their LDL particles.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. a method of analyzing a biological sample obtained from an individual, the method comprising:
   isolating from the sample a very high density, ultra small, lipid-depleted particle comprising:
   a) apolipoprotein B (apoB); and
   b) a cytokeratin 8 polypeptide,
   wherein the isolated particle has an average particle diameter in a range of from about 7.1 nm to about 22 nm, has a density >1.21 g/mL, and has substantially no cholesterol and substantially no triglyceride; and
   detecting a level of the isolated particle,
   wherein a level of the particle that is higher than a normal control level indicates that the individual has an increased risk of cardiovascular disease (CVD) and/or that the individual has an increased risk of mortality due to a CVD.

2. The method of claim 1, wherein the biological sample is blood or a blood fraction.

3. The method of claim 1, further comprising generating a report that provides an indication of the risk that the individual will develop CVD.

4. The method of claim 1, wherein the individual is a human.

5. The method of claim 1, wherein the individual exhibits at least one clinical symptom or sign of cardiovascular disease.

6. The method of claim 1, further comprising communicating to the individual various treatment options based on the results of the detecting step.

7. The method of claim 1, further comprising treating the individual for CVD.

8. The method of claim 1, wherein the individual is an individual receiving a treatment for a cardiovascular disease, and the sample comprises a pre-treatment sample and a post-treatment sample, and the detecting step comprises detecting a
   post-treatment level of the isolated particle and a pre-treatment level of the isolated particle,
   wherein a post-treatment level that is lower than the pre-treatment level indicates that the treatment was efficacious.

9. The method of claim 8, wherein the individual is a human.

10. The method of claim 1, wherein the isolating step comprises subjecting the sample comprising the particle to:
    (i) an immunoaffinity method; and collecting a fraction binding to an antibody specific to apoB in the immunoaffinity method;
    (ii) a density gradient method; and collecting a fraction having a density >1.21 g/mL in the density gradient method; or
    (iii) a gradient gel electrophoresis method; and collecting a fraction advancing beyond an LDL IV standard in the gradient gel electrophoresis method.

11. The method of claim 10, wherein the subjecting step comprises:
    subjecting the sample comprising the particle to the gradient gel electrophoresis method; and
    collecting the fraction advancing beyond the LDL IV standard.

12. The method of claim 1, wherein the detecting comprises contacting the isolated particle with a detectable antibody that binds apolipoprotein B-100 and/or an antibody that binds cytokeratin 8.

13. The method of claim 1, wherein the method further comprises:
  assessing the risk of CVD or mortality due to CVD for the individual based on the individual's detected level of the particle; and
  communicating to the individual the assessment of the risk and/or a suggested treatment regimen for CVD.

14. The method of claim 1, wherein the method further comprises:
  assessing the risk of CVD or mortality due to CVD for the individual based on the individual's detected level of the particle; and
  generating a report that comprises the assessment of the risk, and the detected and control levels of the particle.

15. A kit for assessing risk of cardiovascular disease, the kit comprising:
  a) a reagent that specifically binds apolipoprotein B-100; and
  b) a reagent that specifically binds cytokeratin 8.

16. The kit of claim 15, further comprising an isolated, very high density, ultra small, lipid-depleted particle comprising:
  a) apoB; and
  b) a cytokeratin 8 polypeptide,
  wherein the isolated particle has an average particle diameter in a range of from about 7.1 nm to about 22 nm, has a density >1.21 g/mL, and has substantially no cholesterol and substantially no triglyceride.

17. The kit of claim 15, further comprising instructions for use.

18. The kit of claim 15, wherein each of (a) and (b) is in a separate container.

19. The kit of claim 15, wherein each of (a) and (b) is an antibody.

20. The kit of claim 19, wherein each of the antibodies is immobilized on an insoluble support or is detectably labeled.

21. A method of isolating a very high density, ultra small, lipid-depleted particle, wherein the method comprises:
  subjecting a sample comprising a very high density, ultra small, lipid-depleted particle comprising apoB and a cytokeratin 8 polypeptide to:
  (i) an immunoaffinity method; and collecting a fraction binding to an antibody specific to apoB in the immunoaffinity method;
  (ii) a density gradient method; and collecting a fraction having a density >1.21 g/mL in the density gradient method; or
  (iii) a gradient gel electrophoresis method; and collecting a fraction advancing beyond an LDL IV standard in the gradient gel electrophoresis method,
  thereby isolating the very high density, ultra small, lipid-depleted particle, wherein the particle has an average particle diameter in a range of from about 7.1 nm to about 22 nm, has a density >1.21 g/mL, and has substantially no cholesterol and substantially no triglyceride.

22. The method of claim 21, wherein the subjecting step comprises contacting a sample comprising the particle with an immobilized antibody specific for apoB; and eluting particles bound to the apoB.

23. The method of claim 21, wherein the subjecting step comprises:
  subjecting the sample to a gradient gel electrophoresis method; and
  collecting a fraction advancing beyond an LDL IV standard in the gradient gel electrophoresis method.

24. The method of claim 21, wherein the subjecting step comprises:
  applying the sample to a non-denaturing gradient gel;
  separating components of the sample by applying voltage to the gradient gel; and collecting a fraction advancing beyond an LDL IV standard band in the gradient gel.

25. The method of claim 21, wherein the apoB comprises an amino acid sequence having at least 95% amino acid sequence identity with the amino acid sequence set forth in SEQ ID NO:1.

26. The method of claim 21, wherein the cytokeratin 8 comprises an amino acid sequence having at least 95% amino acid sequence identity with the amino acid sequence set forth in SEQ ID NO:2.

27. The method of claim 21, wherein the isolated particle is at least 85% pure.

28. The method of claim 21, wherein the isolated particle is at least 95% pure.

29. A method of detecting a very high density, ultra small, lipid-depleted particle in a biological sample, wherein the particle comprises apoB and a cytokeratin 8 polypeptide, and wherein the particle has an average particle diameter in a range of from about 7.1 nm to about 22 nm, has a density >1.21 g/mL, and has substantially no cholesterol and substantially no triglyceride, the method comprising:
  a) isolating the particle according to the method of claim 24 to obtain an enriched sample containing the isolated particles;
  b) contacting the enriched sample with a detectable antibody that binds apolipoprotein B-100 and/or an antibody that binds cytokeratin 8; and
  c) detecting binding of the antibody to molecules in the enriched sample.

30. The method of claim 29, wherein the biological sample is obtained from an individual who is being evaluated for possible cardiovascular disease (CVD) or CVD risk.

31. The method of claim 29, wherein the detectable antibody comprises a detectable label.

32. The method of claim 31, wherein the detectable label is selected from the group consisting of: a magnetic bead, a fluorescent dye, a radiolabel, enzyme, a colloidal gold and a colored glass or plastic bead.

\* \* \* \* \*